(12) United States Patent
Mitsuhashi

(10) Patent No.: US 11,852,635 B2
(45) Date of Patent: *Dec. 26, 2023

(54) QUANTIFICATION OF SUBPOPULATIONS OF EXOSOMES AND DIAGNOSIS OF NEUROGENERATIVE DISORDERS

(71) Applicant: Nanosomix, Inc., Aliso Viejo, CA (US)

(72) Inventor: Masato J Mitsuhashi, Irvine, CA (US)

(73) Assignee: Nano Somix, Inc, Aliso Viejo, CA (US)

( * ) Notice: Subject to any disclaimer, the term of this patent is extended or adjusted under 35 U.S.C. 154(b) by 277 days.

This patent is subject to a terminal disclaimer.

(21) Appl. No.: 16/461,787

(22) PCT Filed: Nov. 16, 2017

(86) PCT No.: PCT/US2017/062112
§ 371 (c)(1),
(2) Date: May 16, 2019

(87) PCT Pub. No.: WO2018/094120
PCT Pub. Date: May 24, 2018

(65) Prior Publication Data
US 2019/0361037 A1   Nov. 28, 2019

Related U.S. Application Data

(60) Provisional application No. 62/422,889, filed on Nov. 16, 2016.

(51) Int. Cl.
G01N 33/541    (2006.01)
G01N 33/68     (2006.01)
(Continued)

(52) U.S. Cl.
CPC ...... *G01N 33/6896* (2013.01); *C07K 16/2803* (2013.01); *C12N 5/0619* (2013.01); *G01N 33/541* (2013.01); *G01N 2800/2821* (2013.01)

(58) Field of Classification Search
CPC ............ G01N 33/6896; G01N 33/541; G01N 2800/2821; C07K 16/2803; C12N 5/0619
See application file for complete search history.

(56) References Cited

U.S. PATENT DOCUMENTS

2013/0040318 A1\* 2/2013 Verderio ............ G01N 33/6896
435/7.21
2015/0301058 A1\* 10/2015 Schettini ............ A61K 39/0011
424/193.1

(Continued)

FOREIGN PATENT DOCUMENTS

WO    WO 2015/061634 A2    4/2015

OTHER PUBLICATIONS

International Search Report re PCT/US17/062112, (2018).
(Continued)

*Primary Examiner* — Gailene Gabel
(74) *Attorney, Agent, or Firm* — Sandra P. Thompson; Finlayson Toffer

(57) ABSTRACT

The present invention relates to methods for quantifying subpopulations of exosomes and diagnostic and prognostic methods for neurodegenerative disorders (e.g., Alzheimer's disease). The invention also provides compositions for quantifying subpopulations of exosomes as well as compositions and methods useful for treating Alzheimer's disease and other neurodegenerative disorders.

7 Claims, 31 Drawing Sheets

(51) Int. Cl.
    *C07K 16/28*     (2006.01)
    *C12N 5/0793*     (2010.01)

(56) References Cited

U.S. PATENT DOCUMENTS

2017/0343563 A1\* 11/2017 Goetzl .............. G01N 33/5058
2018/0340945 A1\* 11/2018 Mitsuhashi ............ A61P 25/28
2019/0219578 A1\* 7/2019 Mitsuhashi ........ G01N 33/6896

OTHER PUBLICATIONS

Romain-Daniel Gosselin et al. Extracellular microvesicles from astrocytes contain functional glutamate transporters: regulation by protein kinase C and cell activation. Frontiers in Cellular Neuroscience, 2013, vol. 7, Article 251, pp. 1-15.
Eva-Maria Kramer-Albers et al. Oligodendrocytes secrete exosomes containing major myelin and stress-protective proteins: Trophic support for axons? Proteomics Clin. Appl., 2007, vol. 1, pp. 1446-1461.
Written Opinion of the International Searching Authority re PCT/US17/062112, (2018).

\* cited by examiner

αCD81-beads captured

αCD171-beads captured

Log-R-PE Fluorescence Intensity

QUANTIFICATION OF SUBPOPULATIONS OF EXOSOMES AND DIAGNOSIS OF NEUROGENERATIVE DISORDERS

RELATED APPLICATIONS

This application is a 35 USC § 371 National Stage application of International Application No. PCT/US2017/062112 filed Nov. 16, 2017, now pending; which claims the benefit under 35 USC § 119(e) to U.S. Provisional Patent Application Ser. No. 62/422,889 filed on Nov. 16, 2016. The disclosure of each of the prior applications is considered part of and is incorporated by reference in the disclosure of this application.

FIELD OF THE INVENTION

The present invention relates to methods for quantifying subpopulations of exosomes and diagnostic and prognostic methods for neurodegenerative disorders (e.g., Alzheimer's disease). The invention also provides compositions for quantifying subpopulations of exosomes as well as compositions and methods useful for treating Alzheimer's disease and other neurodegenerative disorders.

BACKGROUND OF THE INVENTION

Exosomes are present in biological samples, such as, for example, plasma and carry various biomarkers that may be used to diagnose medical conditions (e.g. Alzheimer's disease). Normal levels of exosomes in biological samples such as plasma has not been established. Thus, there is a need in the art for methods for quantifying exosomes in biological samples. Additionally, more than 5.4 million Americans and 35 million people worldwide have Alzheimer's disease, the most common form of dementia. Currently, the only definitive way to diagnose Alzheimer's disease is by direct examination of brain tissue after a patient dies. Doctors use brain imaging, evaluation of behavior, psychiatric tests, and other means to diagnose the disease in the patients suspected of having Alzheimer's disease, but none are highly accurate, and many are costly or not practical.

Therefore, there is a need in the art for methods for quantifying exosomes and methods for diagnosing Alzheimer's disease and other neurodegenerative disorders. Additionally, there is a need in the art for compositions for quantifying exosomes as well as compositions and methods useful for treating Alzheimer's disease and other neurodegenerative disorders. The present invention meets this need by providing accurate, noninvasive methods for diagnosing Alzheimer's disease and other neurodegenerative disorders. The present invention further provides novel methods, assays, kits, and compositions for quantifying exosomes in biological samples.

SUMMARY OF THE INVENTION

The present invention provides methods comprising the steps of: (i) obtaining a biological sample comprising exosomes, and (ii) detecting whether a biomarker is present in the sample by contacting the sample with an antibody and detecting binding between the biomarker and the antibody, wherein the biomarker is selected from the group consisting of Synaptosome Associated Protein 25 (SNAP25), Excitatory Amino Acid Transporter 1 (EAAT1), Oligodendrocyte-myelin glycoprotein (OMGP), dopamine receptor 1 (DR1), serotonin receptor 2A (SR2A), serotonin receptor 2C (SR2C), gamma-aminobutyric acid (GABA) B1 receptor, glutamate receptor-1 (GluR-1), opioid receptor (KOR), sleep peptide orexin receptor (OR), and Dopamine transporter (DAT). In some embodiments, the antibody is selected from the group consisting of an anti-SNAP25 antibody, an anti-EAAT1 antibody, an anti-OMGP antibody, an anti-DR1 antibody, an anti-SR2A antibody, an anti-SR2C antibody, an anti-GABAB1 antibody, an anti-GluR-1 antibody, an anti-KOR antibody, an anti-OR antibody, and an anti-DAT antibody. In some embodiments, the biomarker is an exosomal biomarker selected from the group consisting of CD81, CD63, and CD9. In other embodiments the biomarker is a neural biomarker selected from the group consisting of SNAP25, EAAT1, OMGP, DR1, SR2A, SR2C, GABAB1, GluR-1, KOR, OR, and DAT. In other embodiments, the biomarker is selected from the group consisting of a receptor for dopamine, serotonin, GABA, glutamate, opioid, orexin, adrenalin, noradrenalin, acetylcholine, and dopamine transporter. In other embodiments, the methods further comprise quantifying the levels of one or more biomarkers in the biological sample. In still other embodiments, the levels of the one or more biomarkers determines the quantity of exosomes in the biological sample. In other embodiments, the exosomes are selected from the group consisting of neuron-derived exosomes, astrocyte-derived exosomes, oliogodendrocyte-derived exosomes, and microglia-derived exosomes. In other embodiments, the exosomes are selected from the group consisting of pre-synaptic dopaminergic neuron-derived exosome, post-synaptic dopaminergic neuron-derived exosomes, serotonergic neuron-derived exosomes, GABAnergic neuron-derived exosomes, glutamatergic neuron-derived exosomes, and opioid neuron-derived exosomes. In yet other embodiments, the subject has been diagnosed or suspected of having a neurodegenerative disorder. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In some embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid.

The present invention provides methods comprising: (i) obtaining a biological sample comprising exosomes, (ii) detecting whether one or more exosome biomarkers are present in the sample by contacting the sample with one or more antibodies and detecting binding between the one or more exosome biomarkers and the one or more antibodies, wherein the one or more exosome biomarkers are selected from the group consisting of CD81, CD63, and CD9, and (iii) detecting whether one or more neural biomarkers are present in the sample by contacting the sample with one or more antibodies and detecting binding between the one or more neural biomarkers and the one or more antibodies, wherein the one or more neural biomarkers are selected from the group consisting of SNAP25, EAAT1, OMGP, DR1, SR2A, SR2C, GABAB1, GluR-1, KOR, OR, and DAT.

In other embodiments, the present invention provides methods comprising: (i) obtaining a biological sample comprising exosomes, and (ii) determining the amount of at least one exosome biomarker and at least one neural biomarker in the sample. In some embodiments, the exosome biomarker is selected from the group consisting of CD81, CD63, and CD9. In other embodiments, the neural biomarker is selected from the group consisting of SNAP25, EAAT1, OMGP, DR1, SR2A, SR2C, GABAB1, GluR-1, KOR, OR, and DAT. In some embodiments, the exosome biomarker is CD81 and the neural biomarker is SNAP25. In some embodiments, the exosome biomarker is CD81 and the neural biomarker is EAAT1. In some embodiments, the exosome biomarker is CD81 and the neural biomarker is OMGP. In some embodiments, the exosome biomarker is CD81 and the neural biomarker is DR1. In some embodiments, the exosome biomarker is CD81 and the neural biomarker is SR2A. In some embodiments, the exosome biomarker is CD81 and the neural biomarker is SR2C. In some embodiments, the exosome biomarker is CD81 and the neural biomarker is GABAB1. In some embodiments, the exosome biomarker is CD81 and the neural biomarker is GluR-1. In some embodiments, the exosome biomarker is CD81 and the neural biomarker is KOR. In some embodiments, the exosome biomarker is CD81 and the neural biomarker is OR. In some embodiments, the exosome biomarker is CD81 and the neural biomarker is DAT.

In other embodiments, the invention provides methods for determining the levels of brain-derived exosomes in a biological sample comprising, detecting the levels of double positive exosomes in a biological sample, wherein the exosome is positive for at least one exosome biomarker and positive for at least one neural biomarker, thereby determining the levels of brain-derived exosomes. In some embodiments, the exosome marker is selected from the group consisting of CD81, CD63, and CD9. In other embodiments, the neural biomarker is selected from the group consisting of a receptor for dopamine, serotonin, GABA, glutamate, opioid, orexin, adrenalin, noradrenalin, acetylcholine, and dopamine transporter. In other embodiments, the neural biomarker is selected from the group consisting of SNAP25, EAAT1, OMGP, DR1, SR2A, SR2C, GABAB1, GluR-1, KOR, OR, and DAT. The present invention also provides methods for isolating brain-derived exosomes in a biological sample comprising, detecting the levels of double positive exosomes in a biological sample, wherein the exosome is positive for at least one exosome biomarker and positive for at least one neural biomarker, thereby determining the levels of brain-derived exosomes. In some embodiments, the exosome marker is selected from the group consisting of CD81, CD63, and CD9. In other embodiments, the neural biomarker is selected from the group consisting of SNAP25, EAAT1, OMGP, DR1, SR2A, SR2C, GABAB1, GluR-1, KOR, OR, and DAT.

The present invention also provides methods comprising: (i) obtaining a biological sample comprising exosomes, (ii) processing the sample to isolate or enrich the sample for exosomes and (iii) detecting the levels of one or more biomarkers in the biological sample, wherein at least one of the one or more biomarkers is selected from the group consisting of SNAP25, EAAT1, OMGP, DR1, SR2A, SR2C, GABAB1, GluR-1, KOR, OR, and DAT. In some embodiments, the enriching or isolating exosomes from the biological sample comprises: contacting the biological sample with an agent under conditions wherein an exosome present in said biological sample binds to said agent to form an exosome-agent complex; and isolating said exosome from said exosome-agent complex to obtain a sample containing said exosomes, wherein the purity of exosomes present in said sample is greater than the purity of exosomes present in said biological sample. In other embodiments, the agent is an anti-CD81 antibody, an anti-CD63 antibody, an anti-CD9 antibody or an anti-CD171 antibody. In other embodiments, the agent is an anti-SNAP25 antibody, an anti-EAAT1 antibody, an anti-OMGP antibody, an anti-DR1 antibody, an anti-SR2A antibody, an anti-SR2C antibody, an anti-GABAB1 antibody, an anti-GluR-1 antibody, an anti-KOR antibody, an anti-OR antibody, and an anti-DAT antibody. In some embodiments the agent is immobilized on a solid support. In other embodiments, the exosomes are selected from the group consisting of neuron-derived exosomes, astrocyte-derived exosomes, oliogodendrocyte-derived exosomes, and microglia-derived exosomes. In still other embodiments, the subject has been diagnosed or suspected of having a neurodegenerative disorder. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid.

The present invention provides a set of biomarkers for quantifying exosomes in a biological sample, wherein the biomarkers are selected from the group consisting of SNAP25, EAAT1, OMGP, DR1, SR2A, SR2C, GABAB1, GluR-1, KOR, OR, and DAT. In other embodiments, the present invention provides a set of biomarkers for quantifying exosomes in a biological sample, wherein the biomarkers are selected from the group consisting of a dopamine receptor, a serotonin receptor, a GABA receptor, a glutamate receptor, an opioid receptor, an orexin receptor, an adrenalin receptor, a noradrenalin receptor, an acetylcholine receptor, and a dopamine transporter. In some embodiments, the levels of the biomarkers in the set are assayed; and wherein the biomarker level determines the quantity of exosomes in the biological sample. In other embodiments, the exosomes are selected from the group consisting of neuron-derived exosomes, astrocyte-derived exosomes, oliogodendrocyte-derived exosomes, and microglia-derived exosomes. In still other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid.

In other embodiments, the present invention provides a kit for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, the kit comprising one or more agents which specifically binds exosomes, one or more agents which specifically bind a biomarker, one or more containers for collecting and or holding the biological sample, and an instruction for its use, wherein the biomarker is selected from the group consisting of SNAP25, EAAT1, OMGP, DR1, SR2A, SR2C, GABAB1, GluR-1, KOR, OR, and DAT. In some embodiments, the agents are selected from the group consisting of an anti-SNAP25 antibody, an anti-EAAT1 antibody, an anti-OMGP antibody, an anti-DR1 antibody, an anti-SR2A antibody, an anti-SR2C antibody, an anti-GABAB1 antibody, an anti-GluR-1 antibody, an anti-KOR antibody, an anti-OR antibody, and an anti-DAT antibody. In other embodiments, the exosomes are selected from the group consisting of neuron-derived exosomes, astrocyte-derived exosomes, oliogodendrocyte-derived exosomes, and microglia-derived exosomes. In yet other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

In other embodiments, the present invention provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: assaying the level of one or more biomarkers in a biological sample from the subject; and diagnosing or prognosing a neurodegenerative disorder in a subject, identifying a subject at risk of a neurodegenerative disorder, or prescribing a therapeutic regimen or predicting benefit from therapy in a subject having a neurodegenerative disorder based on the levels of the biomarker, wherein at least one of the one or more biomarkers are selected from the group consisting of SNAP25, EAAT1, OMGP, DR1, SR2A, SR2C, GABAB1, GluR-1, KOR, OR, and DAT. In some embodiments, the level of the one or more biomarkers in the biological sample is compared to the level of one or more biomarkers in a control sample and wherein the level of the one or more biomarkers of the biological sample is elevated compared to the control sample. In some embodiments, the level of the one or more biomarkers in the biological sample is compared to the level of one or more biomarkers in a control sample and wherein the level of the one or more biomarkers of the biological sample is decreased compared to the control sample. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In other embodiments, the method further comprises isolating exosomes from the biological samples. In certain embodiments, the isolated exosomes are selected from the group consisting of neuron-derived exosomes, astrocyte-derived exosomes, oliogodendrocyte-derived exosomes, and microglia-derived exosomes. In other embodiments, the exosomes are selected from the group consisting of pre-synaptic dopaminergic neuron-derived exosome, post-synaptic dopaminergic neuron-derived exosomes, serotonergic neuron-derived exosomes, GABAnergic neuron-derived exosomes, glutamatergic neuron-derived exosomes, and opioid neuron-derived exosomes. In other embodiments, the level of one or more biomarkers is the protein, mRNA, or miRNA level of the one or more biomarker. In some aspects, the methods of the present invention further comprise predicting the movement from pre-clinical to the manifestation of a neurodegenerative disorder. In other aspects, the methods of the present invention further comprise predicting outcome or worsening of the neurodegenerative disorder. In yet other aspects, the methods of the present invention comprise preventing Alzheimer's disease. In some aspects, the methods of the present invention further comprise predicting the conversion from mild cognitive impairment to Alzheimer's disease dementia. In other embodiments, the method further comprises measuring the level of one or more biomarkers in the biological sample, wherein at least one of the one or more biomarkers are selected from the group consisting of SNAP25, EAAT1, OMGP, DR1, SR2A, SR2C, GABAB1, GluR-1, KOR, OR, and DAT.

The present invention also provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: isolating exosomes from a biological sample obtained from the subject; and determining the level of one or more biomarkers in the exosomes; wherein an elevated level of the one or more biomarkers in the sample compared to the level of the one or more biomarkers in a control sample is an indication of a neurodegenerative disorder, wherein at least one of the one or more biomarkers is selected from the group consisting of SNAP25, EAAT1, OMGP, DR1, SR2A, SR2C, GABAB1, GluR-1, KOR, OR, and DAT. In some embodiments, the level of the one or more biomarkers in the biological sample is decreased compared to the control sample. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In still other embodiments, the isolated exosomes are selected from the group consisting of neuron-derived exosomes, astrocyte-derived exosomes, oliogodendrocyte-derived exosomes, and microglia-derived exosomes. In other embodiments, the isolating exosomes from a biological sample comprises: contacting the biological sample with an agent under conditions wherein an exosome present in said biological sample binds to said agent to form an exosome-agent complex; and isolating said exosome from said exosome-agent complex to obtain a sample containing said exosome, wherein the purity of exosomes present in said sample is greater than the purity of exosomes present in said biological sample. In other embodiments, the isolating exosomes from a biological sample comprises: isolating exosomes from said biological sample to obtain an exosome sample; contacting the exosome sample with an agent under conditions wherein an exosome present in said exosome sample binds to said agent to form an exosome-agent complex; and isolating said exosome from said exosome-agent complex to obtain a sample containing said exosome, wherein the purity of exosomes present in said sample is greater than the purity of exosomes present in said biological sample. In certain aspects, the agent is an antibody, a lectin, a ligand, a soluble receptor, a binding protein, or an oligonucleotide. In other aspects, the antibody is a polyclonal or monoclonal antibody. In yet other aspects, the antibody is a monoclonal NCAM antibody. In other aspects, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In other aspects, the antibody is a neuron-specific enolase antibody. In other aspects, the antibody is a monoclonal neuron-specific enolase antibody. In other aspects, the antibody is a monoclonal SNAP25 antibody. In other aspects, the antibody is a monoclonal EAAT1 antibody. In other aspects, the antibody is a monoclonal OMGP antibody. In other aspects, the antibody is a monoclonal DR1 antibody. In other aspects, the antibody is a monoclonal SR2A antibody. In other aspects, the antibody is a monoclonal SR2C antibody. In other aspects, the antibody is a monoclonal GABAB1 antibody. In other aspects, the antibody is a monoclonal GluR-1 antibody. In other aspects, the antibody is a monoclonal KOR antibody. In other aspects, the antibody is a monoclonal OR antibody. In other aspects, the antibody is a monoclonal DAT antibody. In other aspects, the antibody is a monoclonal DAT antibody. In other aspects, the antibody is a monoclonal dopamine receptor antibody. In other aspects, the antibody is a monoclonal serotonin receptor antibody. In other aspects, the antibody is a monoclonal GABA receptor antibody. In other aspects, the antibody is a monoclonal glutamate receptor antibody. In other aspects, the antibody is a monoclonal opioid receptor antibody. In other aspects, the antibody is a monoclonal orexin receptor antibody. In other aspects, the antibody is a monoclonal adrenalin receptor antibody. In other aspects, the antibody is a monoclonal noradrenalin receptor antibody. In other aspects, the antibody is a monoclonal acetylcholine receptor antibody. In other aspects, the antibody is a monoclonal dopamine transporter antibody. In other embodiments, the level of one or more biomarkers is the protein, mRNA, or miRNA level of the one or more biomarker.

The present invention provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: obtaining a biological sample from the subject; applying an antibody specific for exosomes to the sample, wherein the presence of the exosome creates an antibody-exosome complex; isolating the antibody-exosome complex; assaying a level of one or more biomarkers in the antibody-exosome complex; and diagnosing or prognosing a neurodegenerative disorder in a subject, identifying a subject at risk of a neurodegenerative disorder, or prescribing a therapeutic regimen or predicting benefit from therapy in a subject having a neurodegenerative disorder based on the levels of the one or more biomarkers. In some embodiments, the antibody-exosome complex is created on a solid phase. In yet other embodiments, the methods further comprise releasing the exosome from the antibody-exosome complex. In certain embodiments, the solid phase is non-magnetic beads, magnetic beads, agarose, or sepharose. In other embodiments, the exosome is released by exposing the antibody-exosome complex to low pH between 3.5 and 1.5. In yet other embodiments, the released exosome is neutralized by adding a high pH solution. In other embodiments, the released exosome is lysed by incubating the released exosomes with a lysis solution. In still other embodiments, the lysis solution contains inhibitors for proteases and phosphatases. In other embodiments, the levels of the one or more biomarkers are normalized by the number of exosomes or values of exosome biomarkers. In certain embodiments, the antibody is a polyclonal or monoclonal antibody. In other embodiments, the antibody is a monoclonal NCAM antibody. In other embodiments, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In other aspects, the antibody is a neuron-specific enolase antibody. In other aspects, the antibody is a monoclonal SNAP25 antibody. In other aspects, the antibody is a monoclonal EAAT1 antibody. In other aspects, the antibody is a monoclonal OMGP antibody. In other aspects, the antibody is a monoclonal neuron-specific enolase antibody. In some embodiments, the exosomes are selected from the group consisting of neuron-derived exosomes, astrocyte-derived exosomes, oliogodendrocyte-derived exosomes, and microglia-derived exosomes. In yet other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the level of one or more biomarkers is the protein, mRNA, or miRNA level of the one or more biomarker.

The present invention provides sets of biomarkers for assessing neurodegenerative disorder status of a subject comprising one or more biomarkers, wherein the levels of the biomarkers in the set are assayed; and wherein the biomarker level determines the neurodegenerative disorder status of the subject with at least 40% specificity, wherein the at least one or more of the set of biomarkers are selected from the group consisting of SNAP25, EAAT1, OMGP, DR1, SR2A, SR2C, GABAB1, GluR-1, KOR, OR, and DAT. In some embodiments, the biomarker level determines the neurodegenerative disorder status of the subject with at least 40%, 50%, 60%, 70%, 75%, 80%, 85%, 90%, 95%, 99%, or 100% specificity. In some embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In yet other embodiments, the methods further comprise assaying the levels of the biomarkers in exosomes from the sample. In other embodiments, the sets of biomarkers of the present invention further comprise one or more biomarkers selected from the group consisting of SNAP25, EAAT1, OMGP, DR1, SR2A, SR2C, GABAB1, GluR-1, KOR, OR, and DAT.

The present invention also provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, the kit comprising one or more agents which specifically binds exosomes, one or more probes or primers for detecting biomarker mRNA or miRNA, one or more containers for collecting and or holding the biological sample, and an instruction for its use, wherein the neurodegenerative disorder is associated with altered biomarker levels and wherein the biomarker is selected from the group consisting of SNAP25, EAAT1, OMGP, DR1, SR2A, SR2C, GABAB1, GluR-1, KOR, OR, and DAT. In some embodiments, the agents are polyclonal or monoclonal antibodies. In other embodiments, the exosomes are selected from the group consisting of neuron-derived exosomes, astrocyte-derived exosomes, oliogodendrocyte-derived exosomes, and microglia-derived exosomes. In yet other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In still other embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the kits further comprise a computer model or algorithm for analyzing the biomarker level in the sample. In some embodiments, the kits of the present invention further comprise one or more agents which specifically bind to one or more biomarkers selected from the group consisting of SNAP25, EAAT1, OMGP, DR1, SR2A, SR2C, GABAB1, GluR-1, KOR, OR, and DAT.

In other embodiments, the invention provides for a method of diagnosing, prognosing, determining, predicting a therapeutic regimen or predicting benefit from therapy for a neurodegenerative disorder, comprising assaying a biomarker level in a sample from the subject for a plurality of biomarkers, wherein the plurality of biomarkers comprises one or more biomarkers selected from SNAP25, EAAT1, OMGP, DR1, SR2A, SR2C, GABAB1, GluR-1, KOR, OR, and DAT; and diagnosing, prognosing, determining progression of the neurodegenerative disorder, predicting a therapeutic regimen or predicting benefit from therapy in a subject having a neurodegenerative disorder based on the levels of the plurality of biomarkers. In one aspect, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the method further comprises assaying the level of one or more biomarkers in the biological sample, wherein at least one of the one or more biomarkers are selected from the group consisting of SNAP25, EAAT1, OMGP, DR1, SR2A, SR2C, GABAB1, GluR-1, KOR, OR, and DAT.

In another embodiment, the present invention provides a method of diagnosing and treating a neurodegenerative disorder in a subject, said method comprising: (a) obtaining a sample from a subject, wherein the sample comprises exosomes; (b) processing the sample to isolate or enrich the sample for the exosomes containing biomarkers; and (c) detecting the level of one or more biomarkers in said exosomes, (d) diagnosing the subject with a neurodegenerative disorder based on the level of the one or more biomarkers in the sample relative to the level in a control sample; and (e) administering an effective amount of a therapeutic agent to the diagnosed subject. In one aspect, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the method further comprises assaying the level of one or more biomarkers in the biological sample, wherein at least one of the one or more biomarkers are selected from the group consisting of SNAP25, EAAT1, OMGP, DR1, SR2A, SR2C, GABAB1, GluR-1, KOR, OR, and DAT. In other embodiments, the exosomes are neuron-derived exosomes, astrocyte-derived exosomes, oliogodendrocyte-derived exosomes, or microglia-derived exosomes.

In some embodiments the invention provides methods of quantifying the levels of brain-derived exosomes comprising, detecting double positive exosomes in a biological sample, wherein the exosomes are positive for one or more exosome biomarkers selected from the group consisting of CD81, CD63, and CD9 and wherein the exosomes are positive for one or more neural biomarkers specific to neurons, astrocytes, or oligodendrocytes, thereby quantifying the levels of brain-derived exosomes in the sample. In some embodiments the one or more neural biomarkers are selected from the group consisting of a receptor for dopamine, serotonin, GABA, glutamate, opioid, orexin, adrenalin, noradrenalin, acetylcholine, and dopamine transporter. In some embodiments the one or more neural biomarkers are selected from SNAP25, EAAT1, OMGP, DR1, SR2A, SR2C, GABAB1, GluR-1, KOR, OR, or DAT. In other embodiments, the methods further comprise capturing the exosomes on a solid support comprising at least one capture reagent attached thereto, wherein the capture reagents bind at least one biomarker from the group consisting of CD81, CD63, and CD9.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

DESCRIPTION OF THE INVENTION

Figure 1A:
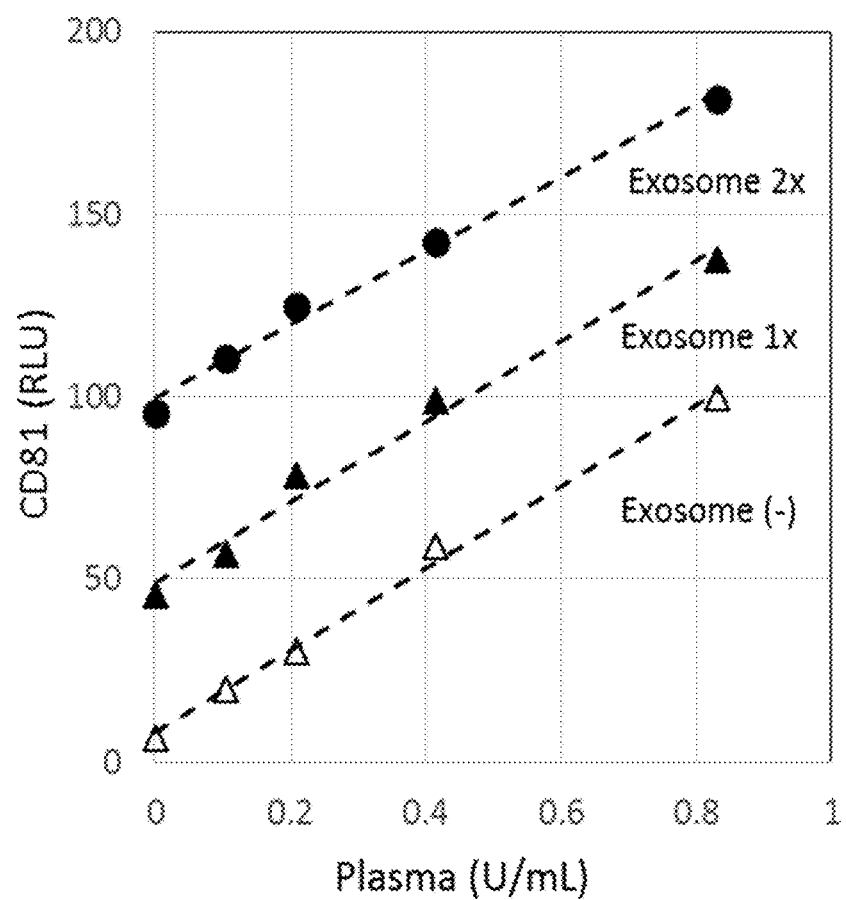
FIGS. 1A-1E set forth data showing Plasma dilution studies with spiked exosomes (Accuracy). A: Total exosome TE), B: SNAP25-based NDE (sNDE), C: CD171-based NDE (cNDE), D: ADE. and E: ODE. Various volumes of standard plasma (Δ) spiked with 2 different doses of isolated total exosomes (▲)(■) were applied to ELISA wells, where anti-CD81 (A-C), anti-EAAT1 (D), or anti-OMGP (E) was previously immobilized. After unbound materials were removed, each well was exposed to labeled antibodies against CD81 (A, D, E), SNAP25 (B), or CD171 (C), followed by 2 step reactions with SA-Ploy HRP and chemiluminescent substrates. Y-axis represents the ELISA readings in relative light units (RLU).
Figure 1B:
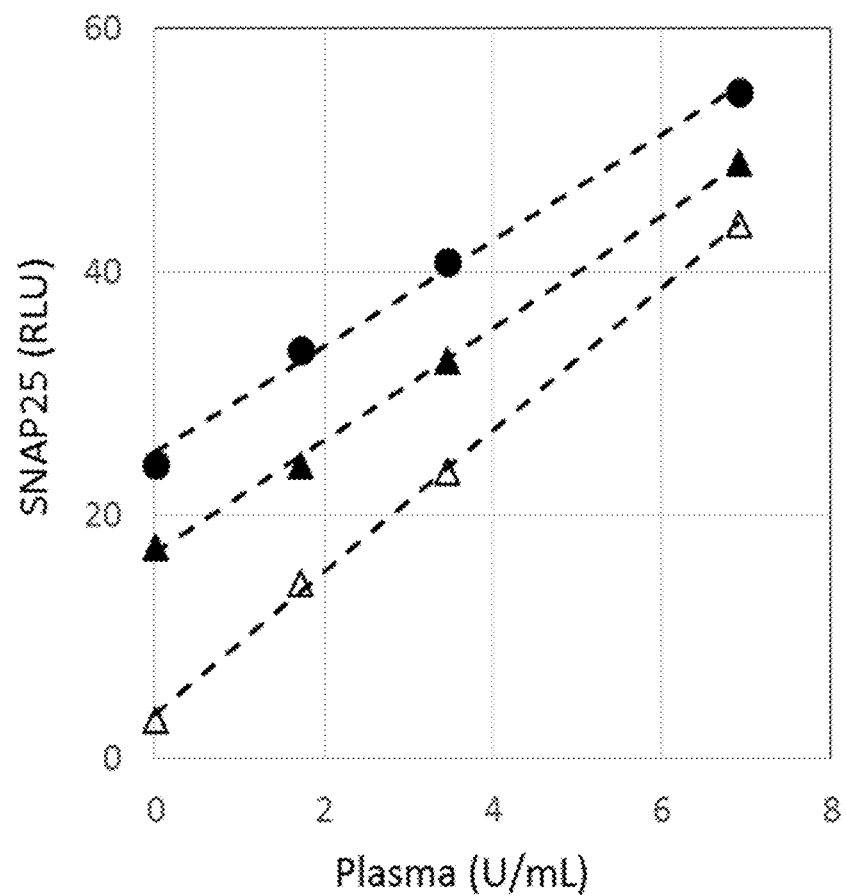
Figure 1C:
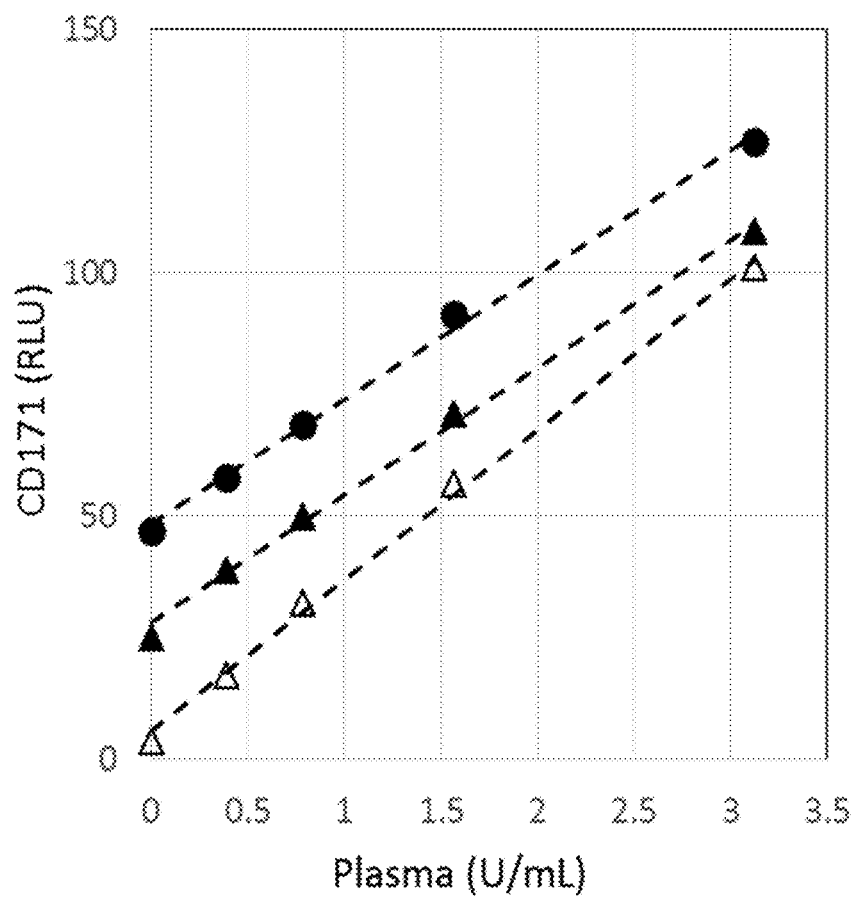
Figure 1D:
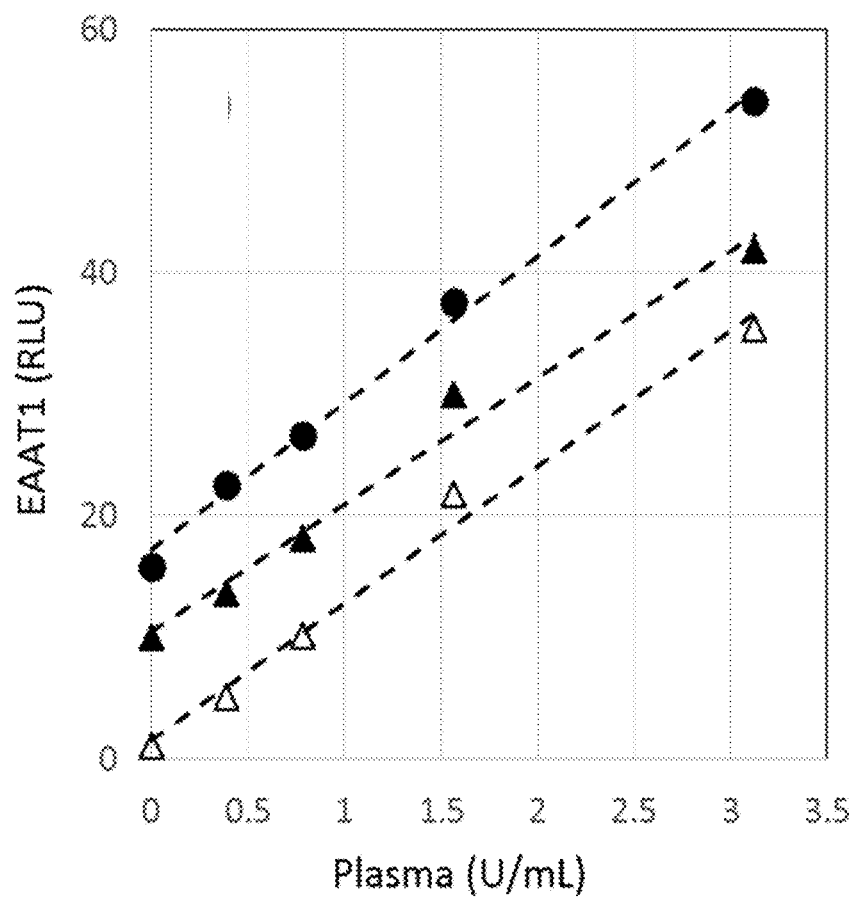
Figure 1E:
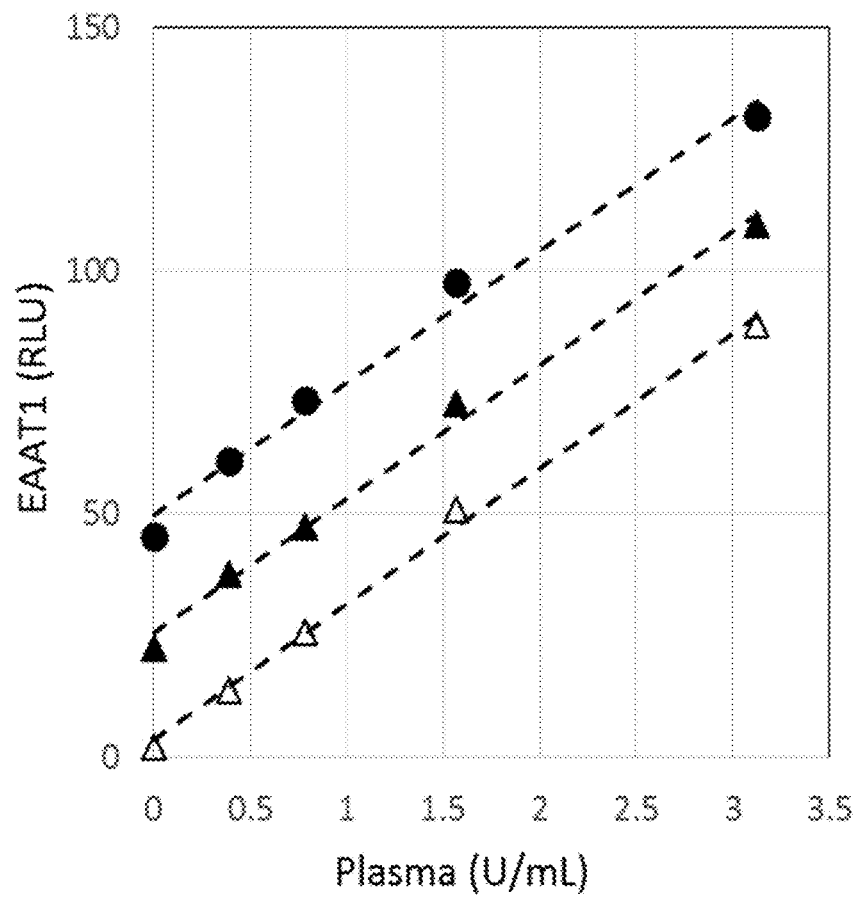

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the discovery that exosomal biomarkers can be assayed to identify subjects having or likely to develop neurodegenerative disorders, including, for example, Alzheimer's disease (AD), multiple sclerosis (MS), and frontotemporal dementia (FTD).

The present invention is based, in part, on the discovery of unexpected increases in certain biomarkers in neuron-derived exosomes present in the circulation of subjects having neurodegenerative disease (e.g., Alzheimer's disease). The present invention demonstrates that exosomal levels of these biomarkers may be assayed to diagnose a neurodegenerative disorder in a subject having a neurodegenerative disease. The present invention further shows that measurement of certain biomarkers in neuron-derived exosomes from a subject may be used to predict the subsequent development of a neurodegenerative disease (e.g., identify a subject at risk of developing a neurodegenerative disorder).

The present invention also provides compositions for use in the methods described herein. Such compositions may include small molecule compounds; peptides and proteins including antibodies or functionally active fragments thereof; and polynucleotides including small interfering ribonucleic acids (siRNAs), micro-RNAs (miRNAs), ribozymes, and anti-sense sequences. (See, e.g., Zeng (2003) Proc Natl Acad Sci USA 100:9779-9784; and Kurreck (2003) Eur J Biochem 270:1628-1644.)

The present invention further provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder. In these embodiments, the kits comprise one or more antibodies which specifically binds exosomes, one or more antibodies which specifically bind a biomarker, one or more containers for collecting and or holding the biological sample, and an instruction for the kits use.

The section headings are used herein for organizational purposes only, and are not to be construed as in any way limiting the subject matter described herein.

Biological Sample

The present invention provides biomarkers and diagnostic and prognostic methods for Alzheimer's disease and other neurodegenerative disorders. The present invention also provides biomarkers for quantifying exosome levels in biological samples. Biomarkers and exosome levels are determined in a biological sample obtained from a subject. In some embodiments, the biological sample of the invention can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Biological samples can also be obtained from other sources known in the art, including whole blood, serum, plasma, urine, interstitial fluid, peritoneal fluid, cervical swab, tears, saliva, buccal swab, skin, cerebrospinal fluid, or other tissues including, for example, brain tissues.

Enrichment or Isolation of Exosomes

Samples can be enriched for exosomes through positive selection, negative selection, or a combination of positive and negative selection. In some embodiments, exosomes are directly captured. In other embodiments, blood cells are captured and exosomes are collected from the remaining biological samples. In some embodiments, the exosomes enriched in the biological samples are neuron-derived exosomes, astrocyte-derived exosomes, oliogodendrocyte-derived exosomes, and microglia-derived exosomes.

Samples can also be enriched for exosomes based on differences in the biochemical properties of exosomes. For example, samples can be enriched for exosomes based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used. In some of the embodiments based on metabolic differences, dye uptake/exclusion measured by flow cytometry or another sorting technology is used. In some of the embodiments based on gene expression, cell culture with cytokines is used. Samples can also be enriched for exosomes based on other biochemical properties known in the art. For example, samples can be enriched for exosomes based on pH or motility. Further, in some embodiments, more than one method is used to enrich for exosomes. In other embodiments, samples are enriched for exosomes using antibodies, ligands, or soluble receptors.

In other embodiments, surface markers are used to positively enrich exosomes in the sample. In other embodiments, NCAM, CD171, CD9, CD63, CD81, neuron-specific enolase, diverse neuron or astrocyte adhesive proteins, microglial CD18/11, or CD3 T cell membrane cell surface markers are used to enrich for exosomes. In other embodiments, SNAP25, EAAT1, OMGP, DR1, SR2A, SR2C, GABAB1, GluR-1, KOR, OR, or DAT are used to enrich for exosomes. In some embodiments, cell surface markers that are not found on exosomes populations are used to negatively enrich exosomes by depleting cell populations. Flow cytometry sorting may also be used to further enrich for exosomes using cell surface markers or intracellular or extracellular markers conjugated to fluorescent labels. Intracellular and extracellular markers may include nuclear stains or antibodies against intracellular or extracellular proteins preferentially expressed in exosomes. Cell surface markers may include antibodies against cell surface antigens that are preferentially expressed on exosomes (e.g., NCAM). In some embodiments, the cell surface marker is a neuron-derived exosome surface marker, including, for example, NCAM or CD171, SNAP25, EAAT1, OMGP, DR1, SR2A, SR2C, GABAB1, GluR-1, KOR, OR, or DAT. In some embodiments, a monoclonal NCAM, CD9, CD63, CD81, neuron-specific enolase, CD171, SNAP25, EAAT1, OMGP, DR1, SR2A, SR2C, GABAB1, GluR-1, KOR, OR, or DAT antibody is used to enrich or isolate exosomes from the sample. In certain aspects, the NCAM, CD9, CD63, CD81, neuron-specific enolase, CD171, SNAP25, EAAT1, OMGP, DR1, SR2A, SR2C, GABAB1, GluR-1, KOR, OR, or DAT antibody is biotinylated. In this embodiment, biotinylated NCAM or CD171 antibody can form an antibody-exosome complex that can be subsequently isolated using streptavidin-agarose resin or beads. In other embodiments, the NCAM, CD9, CD63, CD81, neuron-specific enolase, CD171, SNAP25, EAAT1, OMGP, DR1, SR2A, SR2C, GABAB1, GluR-1, KOR, OR, or DAT antibody is a monoclonal anti-human NCAM, CD9, CD63, CD81, neuron-specific enolase, CD171, SNAP25, EAAT1, OMGP, DR1, SR2A, SR2C, GABAB1, GluR-1, KOR, OR, or DAT antibody.

In some embodiments, enriched exosomes from the biological sample are subsequently enriched for a specific type of exosome (e.g., a subpopulation of exosomes). For example, the biological sample is enriched for exosomes and then the enriched exosomes are subsequently enriched for neural-derived exosomes. In some embodiments, the biological sample is enriched for individual neural cell sources of exosomes. In certain aspects, the neural cell sources of exosomes are microglia, neurons, or astrocytes. In other embodiments, surface markers are used to enrich for a specific type of exosome (e.g., neural-derived exosome). In some embodiments, SNAP25, EAAT1, OMGP, DR1, SR2A, SR2C, GABAB1, GluR-1, KOR, OR, and/or DAT cell surface markers are used to enrich for a specific type of exosome. In some embodiments, cell surface markers that are not found on the exosomes of interest are used to negatively enrich exosomes by depleting unwanted cell populations. Flow cytometry sorting may also be used to further enrich for specific types of exosomes using cell surface markers or intracellular or extracellular markers conjugated to fluorescent labels. Intracellular and extracellular markers may include nuclear stains or antibodies against intracellular or extracellular proteins preferentially expressed in or on the exosomes of interest. Cell surface markers may include antibodies against cell surface antigens that are preferentially expressed on exosomes (e.g., SNAP25, EAAT1, OMGP, DR1, SR2A, SR2C, GABAB1, GluR-1, KOR, OR, and DAT). In some embodiments, the cell surface marker is a neuron-derived exosome surface marker, including, for example, SNAP25. In some embodiments, the cell surface marker is an astrocyte-derived exosome surface marker, including, for example, EAAT1. In some embodiments, the cell surface marker is an oligodendrocyte-derived exosome surface marker, including, for example, OMGP. In some embodiments the cell surface marker is a receptor for dopamine, serotonin, GABA, glutamate, opioid, orexin, adrenalin, noradrenalin, acetylcholine, and/or dopamine transporter. In some embodiments, a monoclonal SNAP25, EAAT1, OMGP, DR1, SR2A, SR2C, GABAB1, GluR-1, KOR, OR, or DAT antibody is used to enrich or isolate exosomes from the sample. In certain aspects, the SNAP25, EAAT1, OMGP, DR1, SR2A, SR2C, GABAB1, GluR-1, KOR, OR, or DAT antibody is biotinylated. In this embodiment, biotinylated SNAP25, EAAT1, OMGP, DR1, SR2A, SR2C, GABAB1, GluR-1, KOR, OR, or DAT antibody can form an antibody-exosome complex that can be subsequently isolated using streptavidin-agarose resin or beads. In other embodiments, the SNAP25, EAAT1, OMGP, DR1, SR2A. SR2C, GABAB1, GluR-1, KOR, OR, or DAT antibody is a monoclonal anti-human SNAP25, EAAT1, OMGP, DR1, SR2A, SR2C, GABAB1, GluR-1, KOR, OR, or DAT antibody.

In other embodiments, exosomes are isolated or enriched from a biological sample comprising: contacting a biological sample with an agent under conditions wherein an exosome present in said biological sample binds to said agent to form an exosome-agent complex; and isolating said exosome from said exosome-agent complex to obtain a sample containing said exosome, wherein the purity of exosomes present in said sample is greater than the purity of exosomes present in said biological sample. In certain embodiments, the agent is an antibody or a lectin. Lectins useful for forming an exosome-lectin complex are described in U.S. Patent Application Publication No. 2012/0077263. In some embodiments, the exosomes are neuron-derived exosomes, astrocyte-derived exosomes, oliogodendrocyte-derived exosomes, or microglia-derived exosomes. In some embodiments, multiple isolating or enriching steps are performed. In certain aspects of the present embodiment, a first isolating step is performed to isolate exosomes from a blood sample and a second isolating step is performed to isolate neural-derived exosomes from other exosomes. In other embodiments, the exosome portion of the exosome-agent complex is lysed using a lysis reagent and the protein levels of the lysed exosome are assayed. In some embodiments, the antibody-exosome complex is created on a solid phase. In yet other embodiments, the methods further comprise releasing the exosome from the antibody-exosome complex. In certain embodiments, the solid phase is non-magnetic beads, magnetic beads, agarose, or sepharose. In other embodiments, the exosome is released by exposing the antibody-exosome complex to low pH between 3.5 and 1.5. In yet other embodiments, the released exosome is neutralized by adding a high pH solution. In other embodiments, the released exosome is lysed by incubating the released exosomes with a lysis solution. In still other embodiments, the lysis solution contains inhibitors for proteases and phosphatases.

Neurodegenerative Disorders

The present invention provides methods for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder.

In some embodiments the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

In some embodiments, the present invention enables a medical practitioner to diagnose or prognose one or more neurodegenerative disorder in a subject. In other embodiments, the present invention enables a medical practitioner to rule out or eliminate one or more neurodegenerative diseases as a diagnostic possibility. In yet other embodiments, the present invention enables a medical practitioner to identify a subject at risk of developing a neurodegenerative disorder. In other embodiments, the present invention enables a medical practitioner to predict whether a subject will later develop a neurodegenerative disorder. In further embodiments, the present invention enables a medical practitioner to prescribe a therapeutic regimen or predict benefit from therapy in a subject having a neurodegenerative disorder.

Biomarkers

Biomarker levels are assayed in a biological sample obtained from a subject having or at-risk of having a neurodegenerative disorder (e.g., Alzheimer's disease). In some embodiments, the biomarker is a receptor for dopamine, serotonin, GABA, glutamate, opioid, orexin, adrenalin, noradrenalin, acetylcholine, and/or dopamine transporter. In some embodiments, the biomarker is SNAP25, EAAT1, OMGP, DR1, SR2A, SR2C, GABAB1, GluR-1, KOR, OR, and/or DAT. Other known neurodegenerative disorder biomarkers may be used in combination with the biomarkers of the present invention. Examples of such biomarkers are provided in US Patent Application Pub. No. 2015/0119278, the contents of which are hereby incorporated by reference.

In some embodiments, biomarker levels of the present invention are measured by determining the quantity or gene expression of the biomarker. In certain embodiments, gene expression changes are measured by determining the expression level of one or more of the genes shown in Table 1. In certain aspects, gene expression of the biomarker is determined using PCR, microarray, or sequencing. In some embodiments, the expression level of the biomarker is determined by measuring the mRNA or miRNA level of the biomarker.

One of ordinary skill in the art has several methods and devices available for the detection and analysis of the markers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of neurodegenerative disorders (e.g., Alzheimer's disease). Markers of such disorders are typically substances found in a bodily sample that can be measured. The measured amount can correlate to underlying disorder or disease pathophysiology, presence or absence of a neurodegenerative disorder, probability of a neurodegenerative disorder in the future. In patients receiving treatment for their condition the measured amount will also correlate with responsiveness to therapy. In some embodiments, an increase in the level of one or more biomarkers of the present invention is indicative of a first neurodegenerative disorder and a decrease in the level of the same one or more biomarkers is indicative of a second neurodegenerative disorder. Accordingly, the methods of the present invention are useful for the differential diagnosis of neurodegenerative disorders.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present invention may be used in clinical assays to diagnose or prognose a neurodegenerative disorder in a subject, identify a subject at risk of a neurodegenerative disorder, and/or for prescribing a therapeutic regimen or predicting benefit from therapy in a subject having a neurodegenerative disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a neurodegenerative disorder in a subject, identifying a subject at risk of a neurodegenerative disorder, or for prescribing a therapeutic regimen or predicting benefit from therapy in a subject having a neurodegenerative disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 1000%.

Compositions

Compositions useful in the methods of the present invention include compositions that specifically recognize a biomarker associated with a neurodegenerative disorder, wherein the biomarker is SNAP25, EAAT1, OMGP, DR1, SR2A, SR2C, GABAB1, GluR-1, KOR, OR, and DAT. In yet other embodiments, the composition is selected from the group consisting of a peptide, a nucleic acid, an antibody, and a small molecule.

In certain embodiments, the present invention relates to compositions that specifically detect a biomarker associated with a neurodegenerative disorder. As detailed elsewhere herein, the present invention is based upon the finding that SNAP25, EAAT1, OMGP, DR1, SR2A, SR2C, GABAB1, GluR-1, KOR, OR, and DAT are specific biomarkers for subpopulations of exosomes that may be used in the diagnosis of neurodegenerative disorders. In some embodiments, the compositions of the present invention specifically bind to and detect SNAP25, EAAT1, OMGP, DR1, SR2A, SR2C, GABAB1, GluR-1, KOR, OR, and DAT. In other embodiments, the compositions of the present invention specifically bind to and detect a receptor for dopamine, serotonin, GABA, glutamate, opioid, orexin, adrenalin, noradrenalin, acetylcholine, and/or dopamine transporter.

In some embodiments, the composition comprises an antibody, where the antibody specifically binds to a biomarker or exosomes of the invention. The term "antibody" as used herein and further discussed below is intended to include fragments thereof which are also specifically reactive with a biomarker or exosome (e.g., exosome). Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an exosome or a biomarker of the present invention, including, for example, neuron-derived exosomes, astrocyte-derived exosomes, oliogodendrocyte-derived exosomes, SNAP25, EAAT1 and OMGP. In some embodiments the neuron-derived exosomes are pre-synaptic dopaminergic neuron-derived exosomes, or post-synaptic dopaminergic, serotonergic, GABAnergic, glutamatergic, and opioid neuron-derived exosomes.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a neurodegenerative disorder. As detailed elsewhere herein, the present invention is based upon the findings that SNAP25, EAAT1, OMGP, DR1, SR2A, SR2C, GABAB1, GluR-1, KOR, OR, and DAT are cell surface markers for specific subpopulations of exosomes. Therefore, in one embodiment, the present invention provides compositions that are useful for detecting and/or quantifying subpopulations of exosomes.

Methods of Treatment

The present invention provides methods of treating a neurodegenerative disorder in a subject, comprising detecting SNAP25, EAAT1, OMGP, DR1, SR2A, SR2C, GABAB1, GluR-1, KOR, OR, and/or DAT in a biological sample from the subject and administering to the subject an effective amount of a composition to treat the neurodegenerative disorder. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid.

Kits

Another aspect of the invention encompasses kits for detecting or monitoring a neurodegenerative disorder in a subject. A variety of kits having different components are contemplated by the current invention. Generally speaking, the kit will include the means for quantifying one or more biomarkers in a biological sample obtained from the subject. In another embodiment, the kit will include means for collecting a biological sample, means for quantifying one or more biomarkers in the biological sample, and instructions for use of the kit contents. In certain embodiments, the kit comprises a means for enriching or isolating exosomes in a biological sample. In further aspects, the means for enriching or isolating exosomes comprises reagents necessary to enrich or isolate exosomes from a biological sample. In certain aspects, the kit comprises a means for quantifying the amount of a biomarker or a specific type of exosome (e.g., neural-derived exosome). In further aspects, the means for quantifying the amount of a biomarker comprises reagents necessary to detect the amount of the biomarker.

TABLE 1

| Gene | Entrez Gene Name | Location |
| --- | --- | --- |
| Synaptosome Associated Protein 25 | SNAP25 | Chromosome 20, NC_000020.11 (10218694 . . . 10307420) |
| Excitatory Amino Acid Transporter 1 | EAAT1 | Chromosome 5, NC_000005.10 (36606355 . . . 36688334) |
| Oligodendrocyte-myelin glycoprotein | OMGP | Chromosome 17, NC_000017.11 (31294650 . . . 31297362, complement) |

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1: Isolation and Quantification of Subpopulations of Exosomes from Biological Samples Specific subpopulations of exosomes were isolated and quantified from biological samples as follows. ELISA assays were performed using white ELISA plates (Coster, Corning, NY), ELISA coating buffer, and ELISA wash buffer (BioLegend, San Diego, CA). Antibodies included anti-CD81 (BD Pharmigen, San Jose, CA), anti-CD63 (Sino Biological, North Wales, PA), and anti-SNAP25 (Santa Cruz Biotechnology, Dallas TX). Biotinylated antibodies included anti-CD81 (LS Bio, Seattle, WA, and MBL, Nagoya, Aichi, Japan), anti-CD171 (eBioscience, San Diego, CA), and anti-SNAP25 (Thermo Fisher Waltham, MA). Unconjugated and biotinylated antibodies against EAAT1 and OMGP (Bioss antibodies, Woburn, MA) were also utilized. Additional materials included normal mouse IgG (Santa Cruz Biotechnology, Dallas TX), ExoQuick (System Biosciences, Palo Alto, CA), human plasma (Innovative Research, Novi, MI; Precision Med, San Diego, CA; BioReclamation IVT, Chestertown, MD), tween-20 (Sigma-Aldrich, St. Louis, MO), EZ-Link Sulfo-NHS-Biotin, Zebra spin columns, phosphate buffered saline (PBS), 10% bovine serum albumin (BSA), blocker casein, streptavidin (SA) Poly-HRP, HRP substrate Super Signal (Thermo Fisher), human neuroblastoma cell line (SK-N-SH, RIKEN BRC, Tsukuba, Ibaraki, Japan), and N2 supplement (Wako Pure Chemicals Industries, Osaka, Japan).

Figure 5:
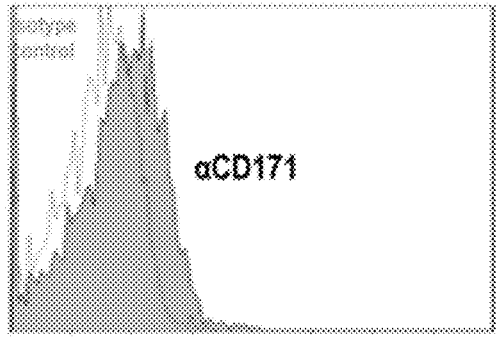
FIG. 5 sets forth data showing flow cytometry profiles of exosomes prepared from SK-N-SH cells culture supernatant.
Figure 5:
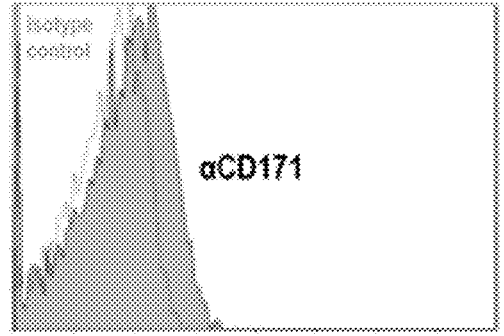
Figure 5:
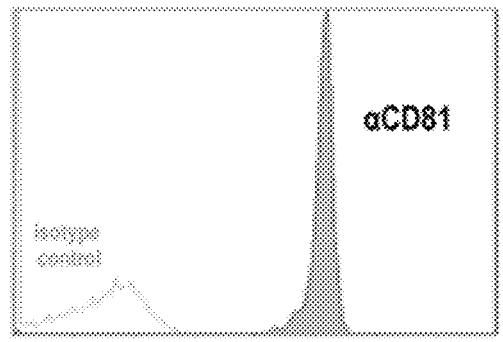
Figure 5:
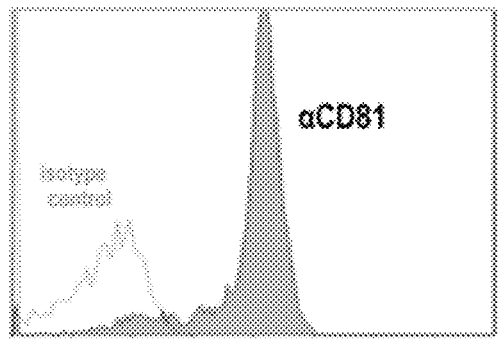

Total exosomes were prepared from various human plasma and culture supernatants using ExoQuick, and suspended in PBS. SK-N-SH cells were cultured in the presence of $1\times10^{-5}$ M all-trans retinoic acid, according to the methods of Hartley et al (10), followed by 7 days of culture in serum free Ham's F-12/Dulbecco's modified Eagle's medium with N2 supplement. Culture supernatants were collected, and aliquots were stored in −80° C. freezer. Dual expression of CD81 and CD171 surface markers were confirmed by flow cytometry (FIG. 5).

Various concentrations of antibodies were suspended in 1×ELISA coating buffer, and 50 μL was dispensed into each well of white ELISA strips. Strips were then incubated in a refrigerator overnight with constant shaking at 700 rpm. After each well was washed with 1× wash buffer once, 75 μL of blocker casein supplemented with 1% BSA was added, and incubated at room temperature for 1 hour with constant shaking at 700 rpm. After incubation, each well was washed with 1× wash buffer twice, and stored in a refrigerator until use.

Antibodies were biotinylated according the protocol of EZ-Link Sulfo-NHS-Biotin (Thermo), and free biotin was removed by applying the samples to spin columns.

Since 50 μL of antibodies were used for immobilization, ELISA was performed in the final volume of 40 μL. Standards and samples were suspended in 40 μL PBS, applied to ELISA wells, and incubated in a refrigerator overnight with constant shaking at 700 rpm. After each well was washed with 1× washer buffer twice, 40 μL PBS supplemented with 1% tween 20 (tPBS), 1% BSA, biotinylated antibodies, and mouse IgG (4 μg/mL) were added into each well, then incubated at room temperature for 1 hour with constant shaking at 700 rpm. After each well was washed with 1× washer buffer twice, 40 μL tPBS-BSA supplemented with blocker casein (5%) and SA Poly-HRP (1/16,000 dilution) were added into each well, then incubated at room temperature for 30 min with constant shaking at 700 rpm. After each well was washed with 1× washer buffer 3 times, 50 μL Super Signal HRP substrate was added into each well, covered with aluminum foil, then incubated at room temperature for 4 min with constant shaking at 700 rpm. Chemiluminescence signals (relative light units (RLU)) were determined in a luminometer (DSL Active GLO (ANSH lab Webster, TX)) with software, Ansh Lite DRS v.12.

Results

Figure 6A:
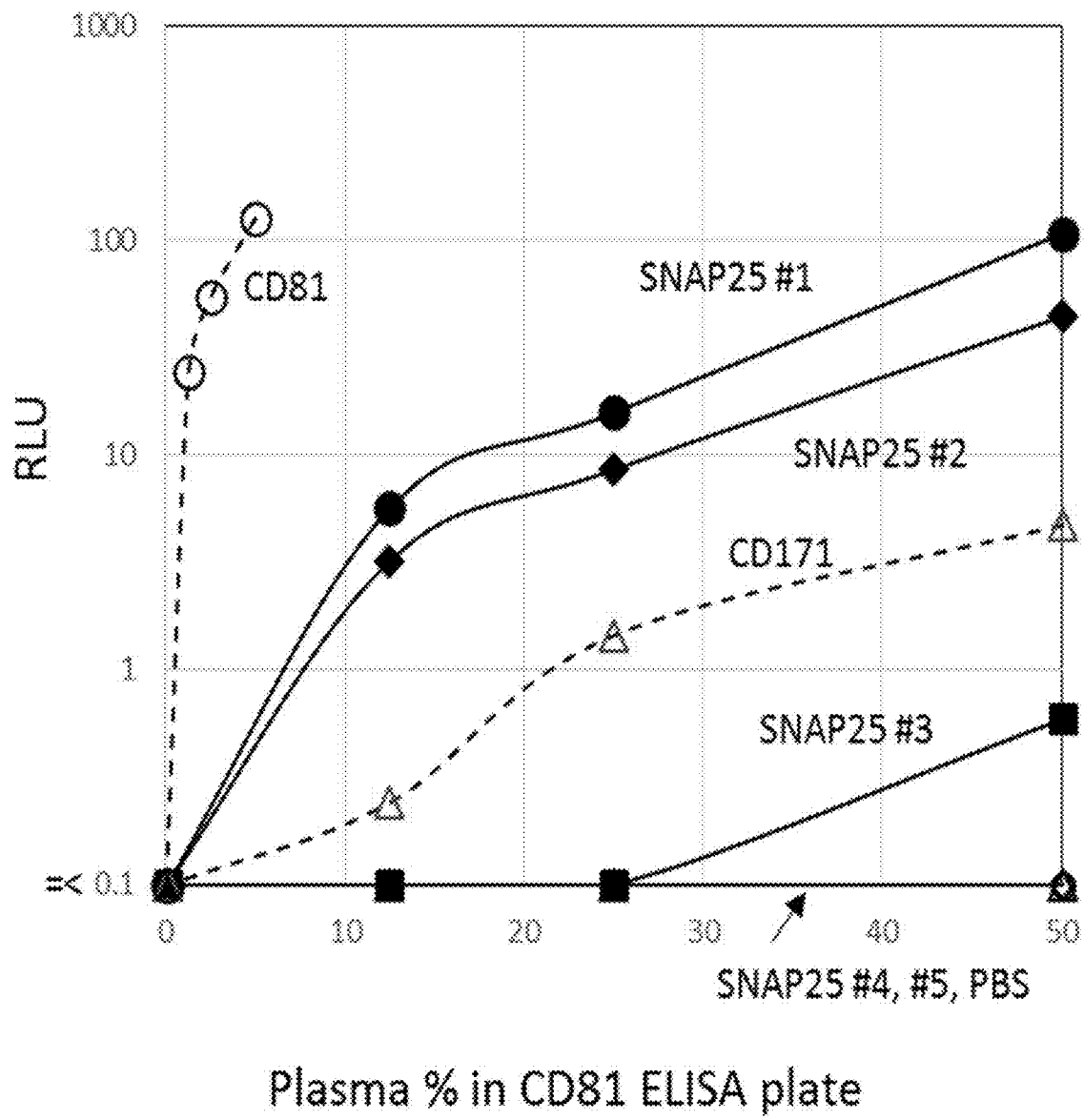
FIGS. 6A and 6B sets forth data showing screening of suitable monoclonal antibodies. Various volumes of plasma were applied to anti-CD81- (A) or anti-CD63-immobilized ELISA wells (B) followed by the reaction with various biotinylated antibodies.
Figure 6B:
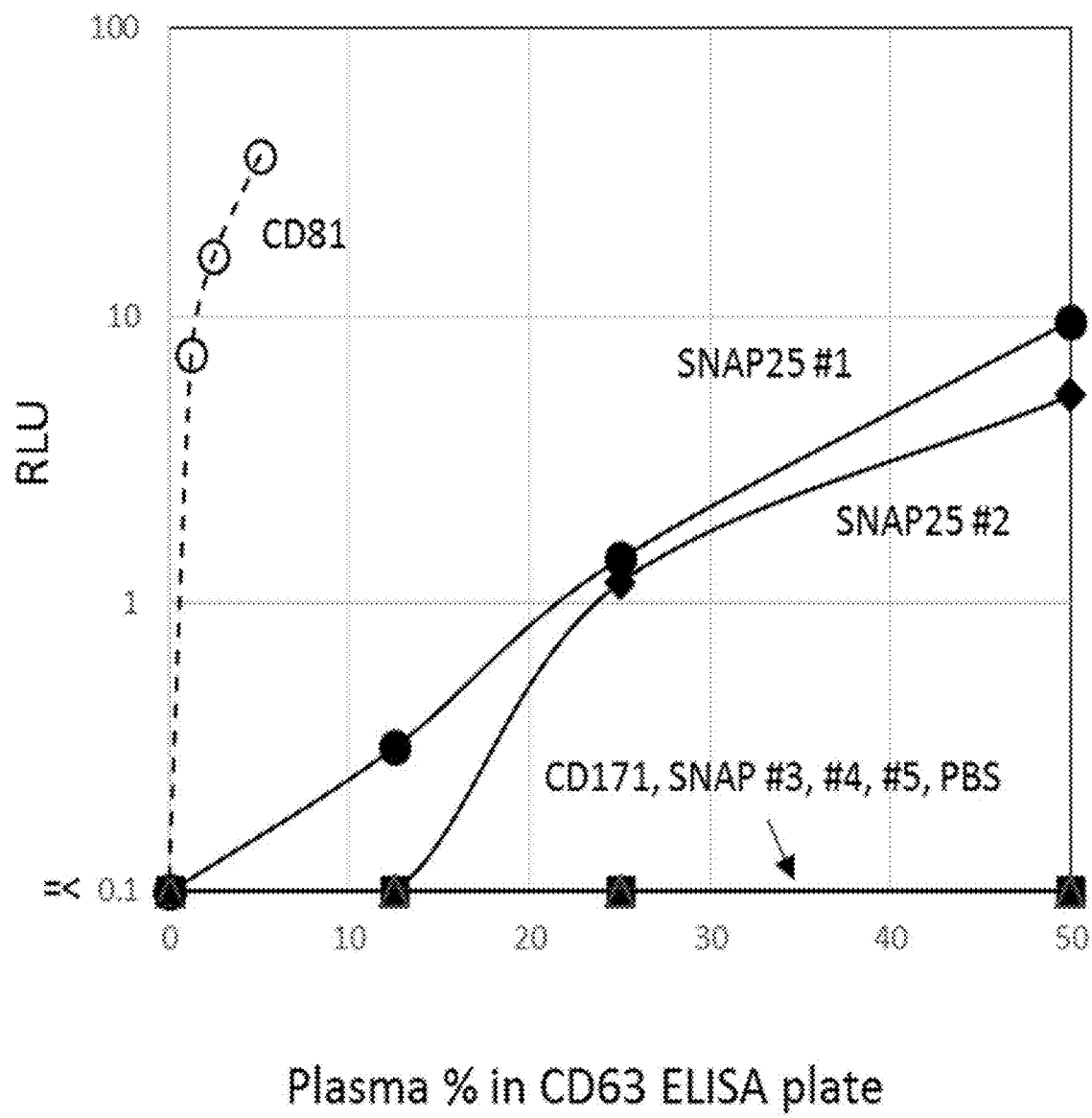

Plasma samples were applied to ELISA wells where anti-CD81 or anti-CD63 antibodies were previously immobilized. After unbound materials were removed, each well was exposed to various biotinylated antibodies, followed by SA Poly-HRP reaction and development of chemiluminescent signals. As shown in FIG. 6 as an example of our screening tests, we first found that anti-CD81 demonstrated better results than anti-CD63. Among many monoclonal antibodies, we discovered very potent anti-SNAP25 and anti-CD171 antibodies. To avoid epitope-to-epitope variation, we used polyclonal antibodies against EAAT1 and OMGP, and found that both antibodies were highly reactive to plasma samples on anti-CD81-immobilized wells. We also switched antibody combinations by immobilizing anti-SNAP25, CD171, EAAT1, and OMGP, then probed with biotinyated anti-CD81. The results were quite equivalent, but anti-EAAT1 and OMGP-immobilized wells showed slightly better performance by increasing signal-to-noise ratio. Thus, we used anti-CD81-immobilized strips for the quantification of total exosome (TE) (anti-CD81 probe) and 2 kinds of NDEs [anti-SNAP25 (sNDE) and anti-CD171 (cNDE)], and anti-EAAT1 and OMGP-immobilized strips (anti-CD81 probe) for the quantification of ADE and ODE.

The assay specificity is based on the combination of exosome marker CD81 and brain markers SNAP25, CD171, EAAT1, and OMGP. As shown in FIG. 6, many antibodies and the no biotin control showed no signals even after a large quantity of plasma was applied. The strong signals were only derived from appropriate antibody combinations, indicating that the ELISA system is specific to two antibody combinations. Specificity of each antibody used in this study was characterized in the package insert of the products.

Unlike conventional sandwich ELISA, recombinant proteins or peptides are not applicable to the quantification standard, because these materials do not express 2 different target epitopes. Thus, we obtained 50 mL of plasma from a single donor to be used as a quantification standard, arbitrarily assigned 100 U/mL, and prepared multiple aliquots which were stored frozen at −80° C. freezer. Each aliquot was used in subsequent studies.

As shown in FIG. 1, ELISA signals for TE, sNDE, cNDE, ADE, and ODE increased linearly in proportion to the amount of standard plasma applied. When 2 different concentrations of total exosome suspension were spiked into standard plasma, RLU shifted upward in parallel with all analytes, indicating that the recovery of exosomes was consistent.

Figure 2A:
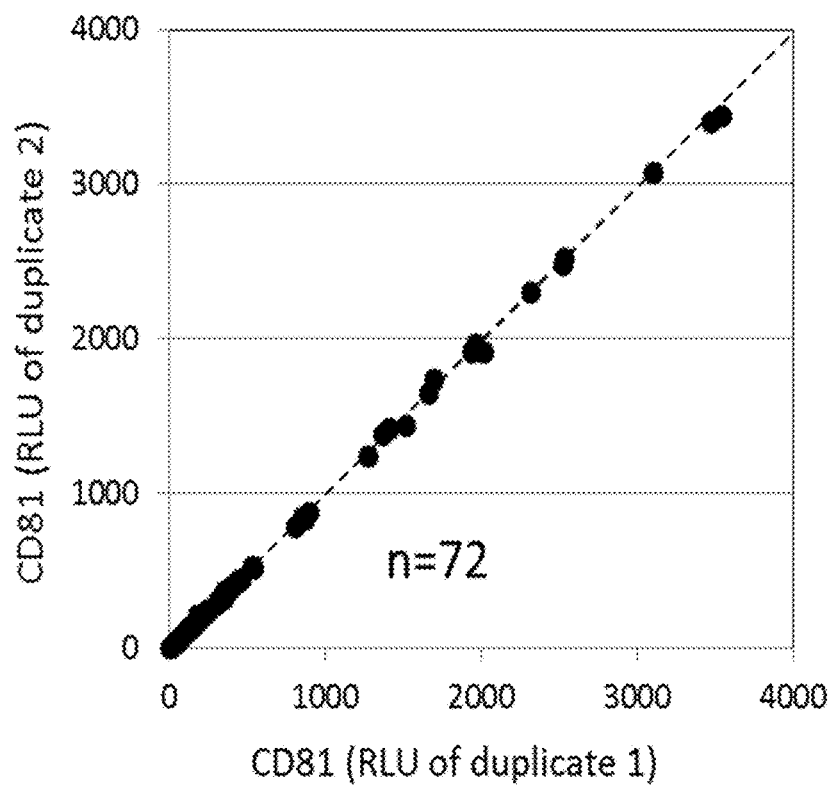
FIGS. 2A-2F set forth data showing intra- and inter-assay variation of ELISA (Precision). A: TE, B: sNDE, C: cNDE, D: ADE, and E: ODE. TE, sNDE, cNDE, ADE, and ODE were analyzed in 72 plasma samples in duplicate. ELISA readings (RLU) of duplicate samples were plotted in X-Y graphs with 45° dotted line. F. Inter-assay variation. TE, sNDE, cNDE, ADE, and ODE (different symbols) were analyzed in 8 different plasma samples in 2 separate experiments. RLU were converted to U/mL and plotted in X-Y graphed with 45° dotted line.
Figure 2B:
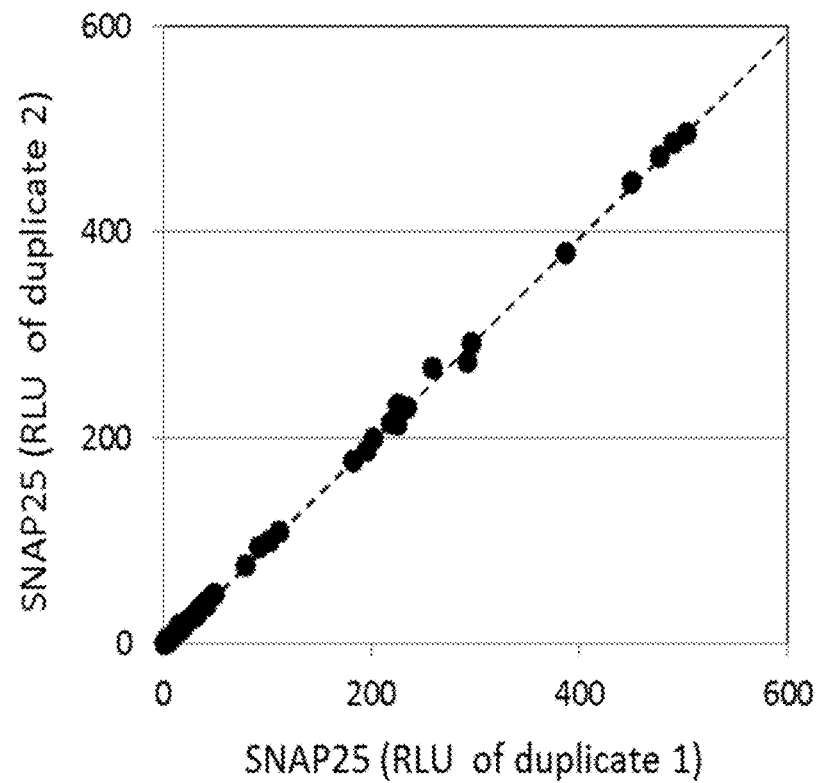
Figure 2C:
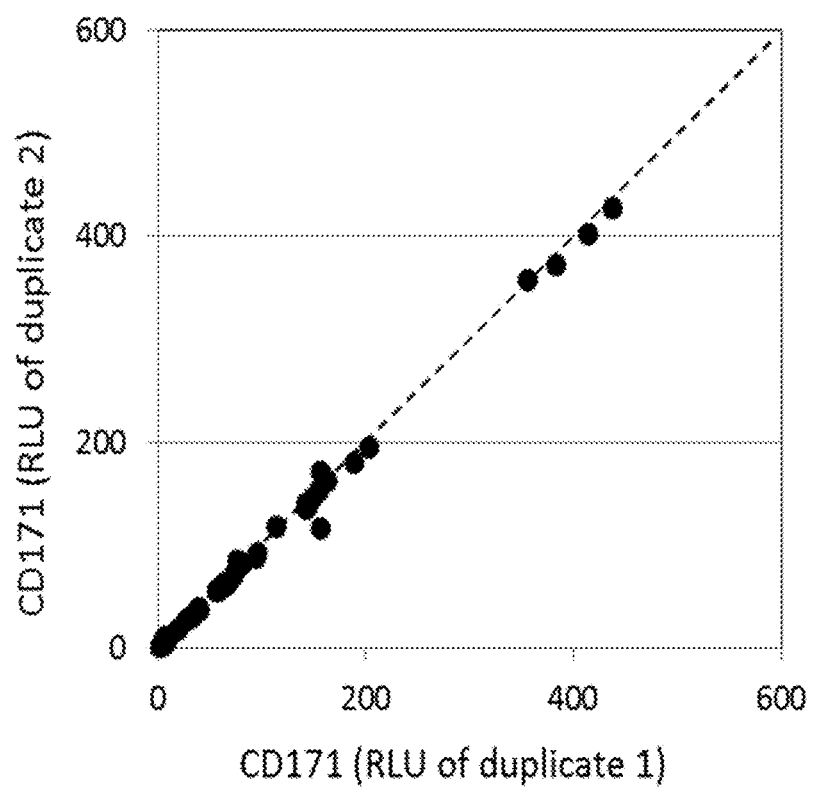
Figure 2D:
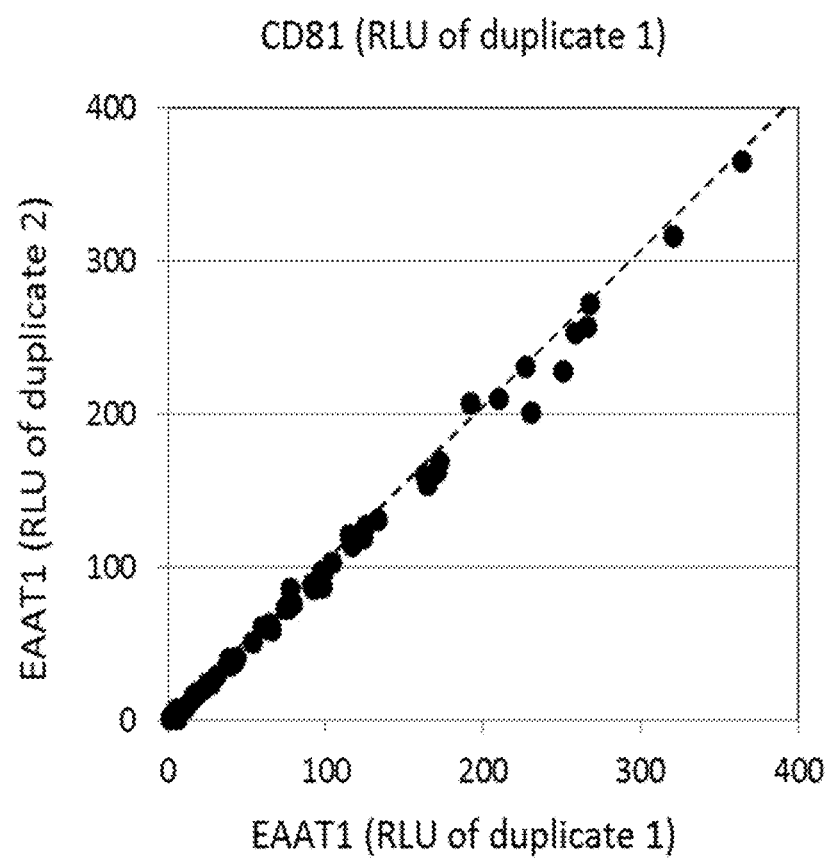
Figure 2E:
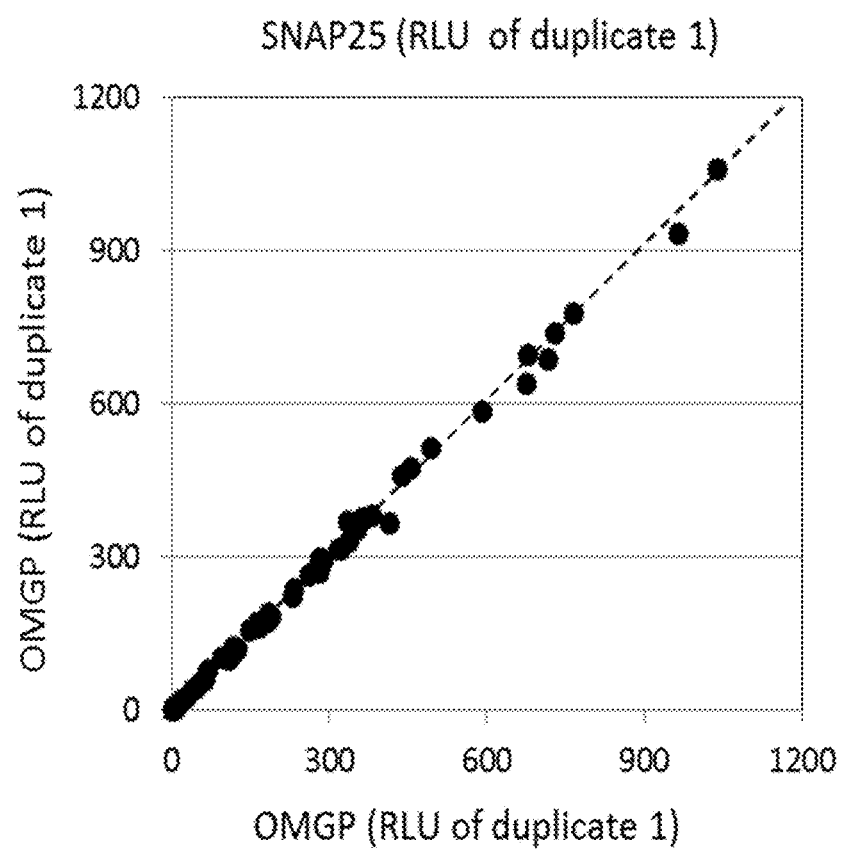
Figure 2F:
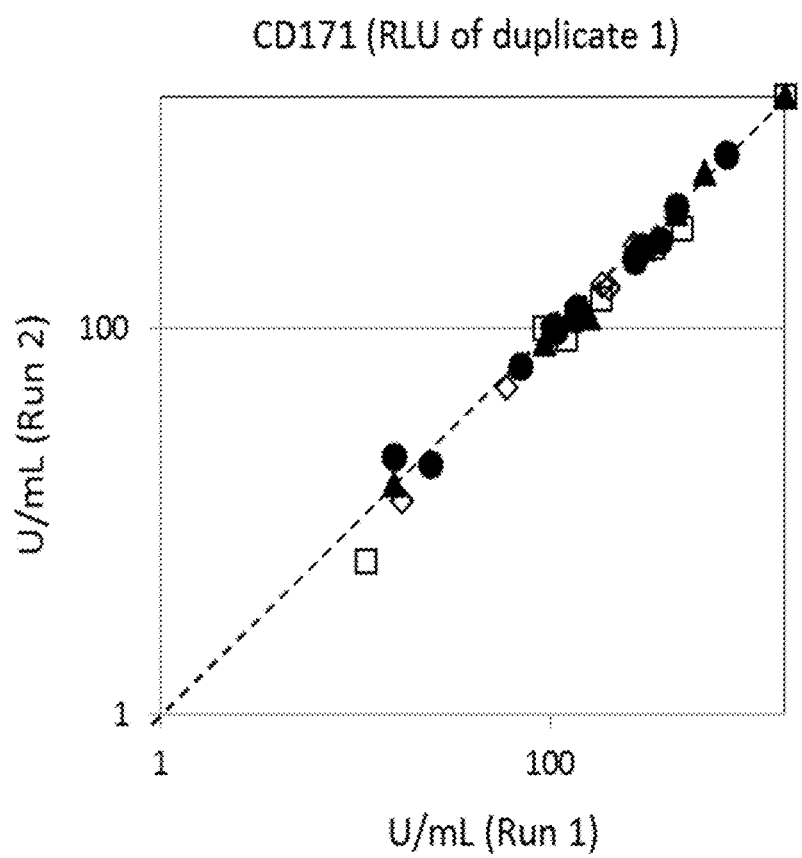
Figure 3A:
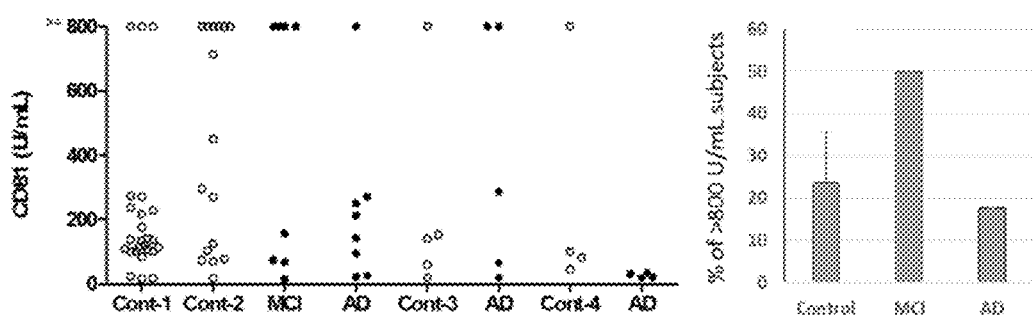
FIGS. 3A-3E set forth data showing plasma levels of TE and each subset of brain-derived exosomes in control subjects and patients with MCI and AD. A: TE, B: sNDE, C: cNDE, D: ADE, and E: ODE. Cont-1 (n=8, 3 separate experiments), 3 (n=5), and 4 (n=4) are control plasmas obtained from 3 different commercial sources. AD in set 2 (n=5) and 3 (n=4) are plasma samples of age- and gender-matched AD patients. Set 1 (8 each of MCI and AD, and 16 age- and gender-matched controls). Values exceeding the highest standard are plotted at the top. a-e. % of subjects exceeded upper detection limit. Four control data were combined and the mean+standard deviation is shown. Statistical analysis was performed by Mann-Whitney U-test.
Figure 3B:
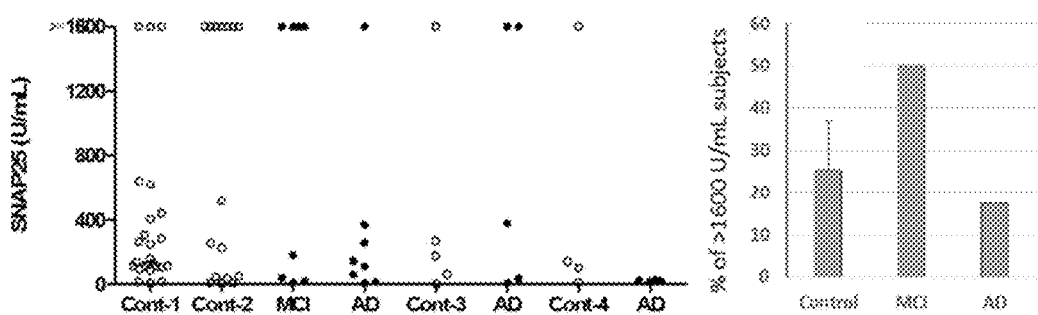
Figure 3C:
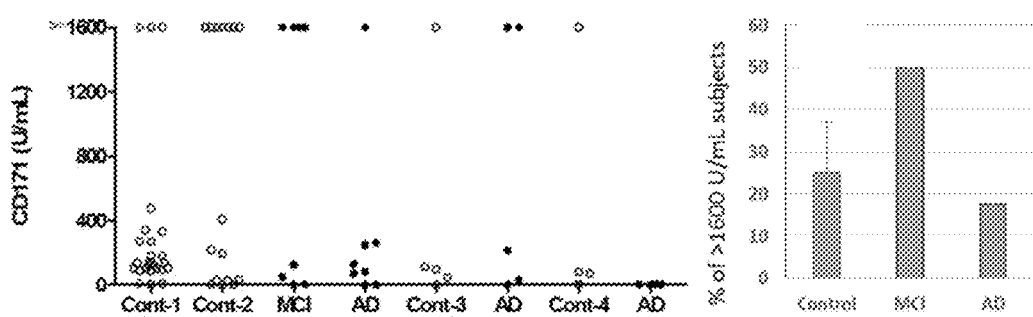
Figure 3D:
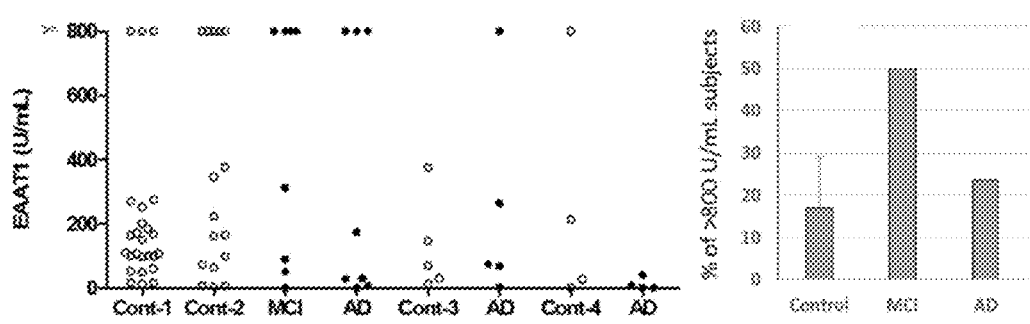
Figure 3E:
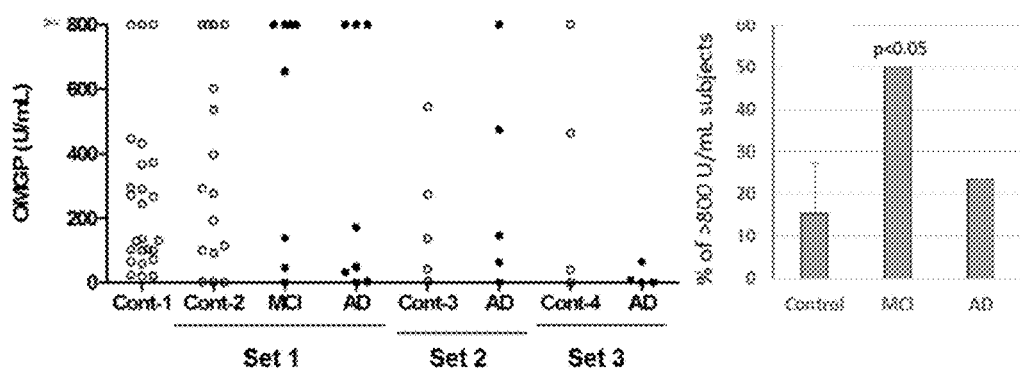
Figure 4A:
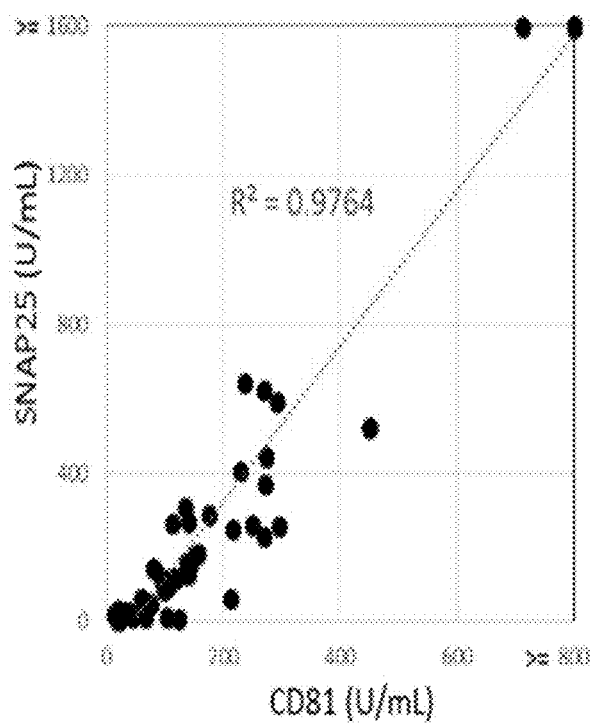
FIGS. 4A-4H set forth data showing correlation among plasma levels of TE and each subset of brain-derived exosomes. A: TE vs sNDE (A), cNDE (B), ADE (C), ODE (D), sNDE vs cNDE (D), ADE (E), ODE (F), and ADE vs ODE (G).
Figure 4B:
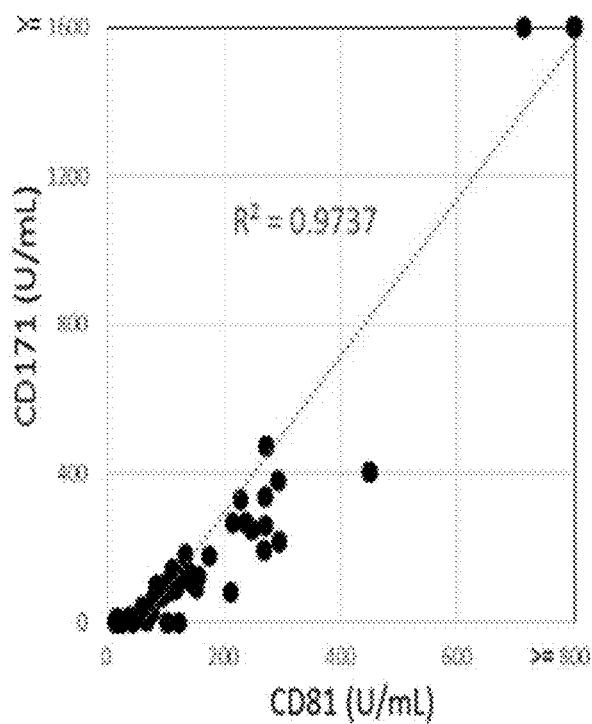
Figure 4C:
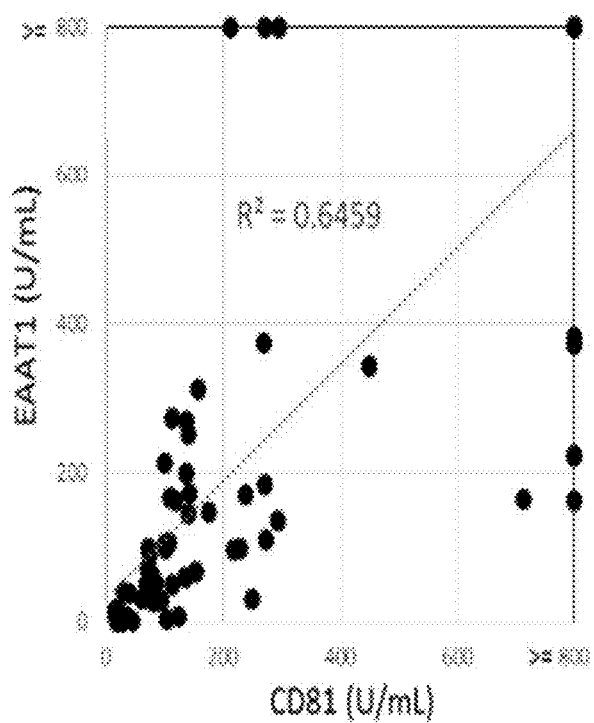
Figure 4D:
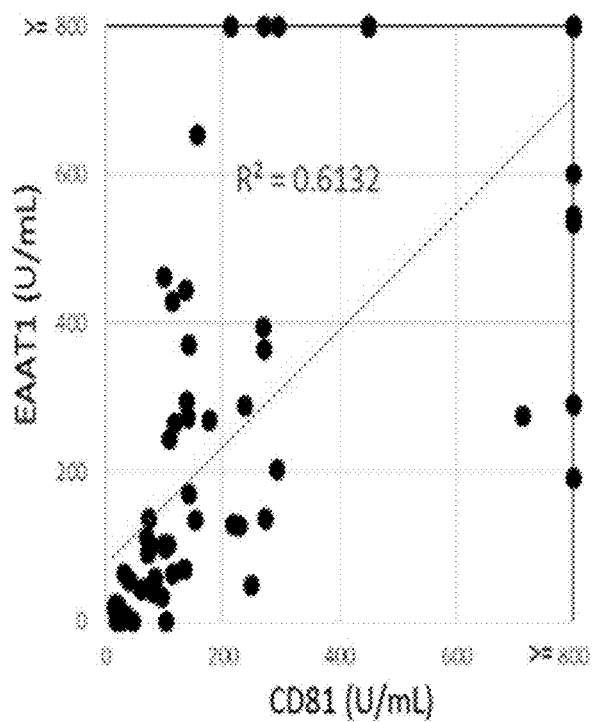
Figure 4E:
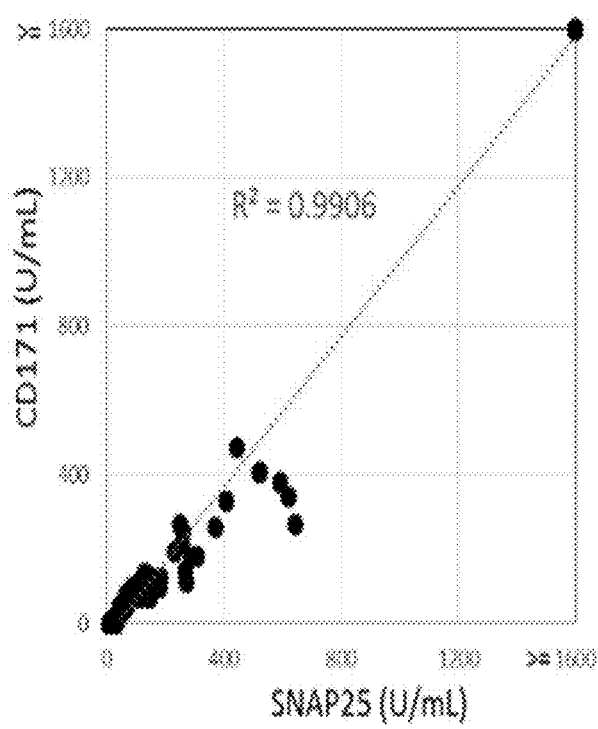
Figure 4F:
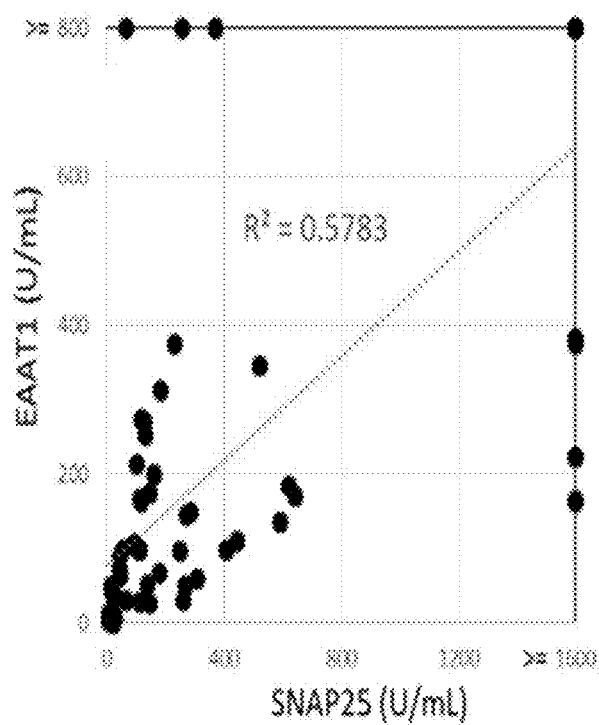
Figure 4G:
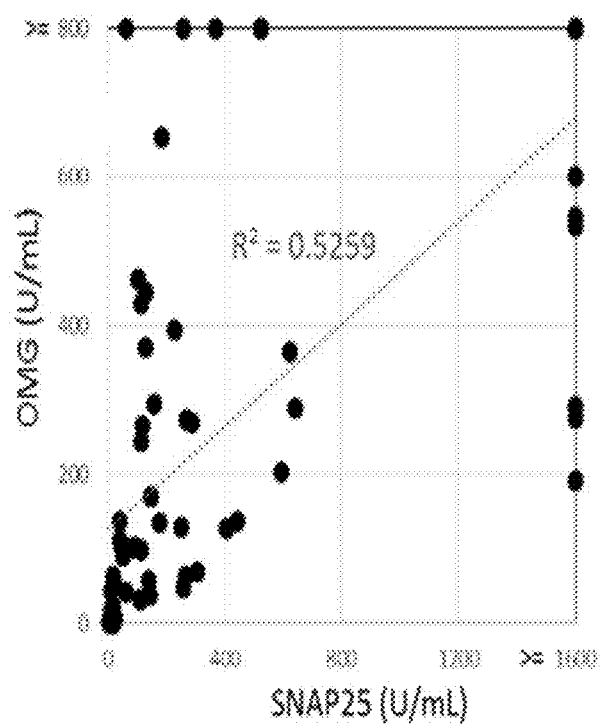
Figure 4H:
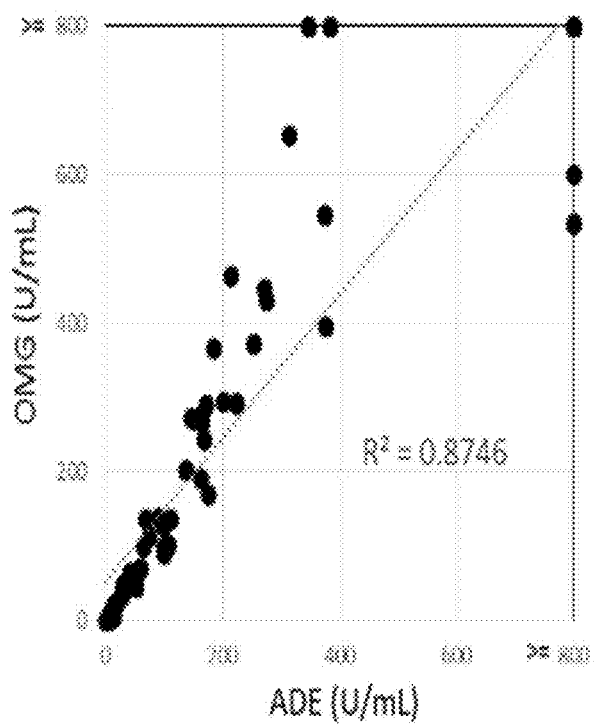

Assay precision is shown in FIG. 2A-E which shows intra-assay variation of duplicate samples from 72 plasma samples used in FIG. 3 (A-E) as well as inter-assay variation of 2 separate determinations of 8 different plasma samples (FIG. 2F). Both intra- and inter-assay variation were minimal.

Plasma samples were diluted 8-fold in PBS, and 5-20 μL were used for each ELISA in duplicate. The required plasma volume for all 5 analytes was as small as 14 μL. The first control group was healthy control plasma obtained from a commercial source (Innovative Research) (n=8) with multiple determinations. Set 1 included 16 age-gender matched controls and 8 each of MCI and AD. Set 2 included 5 each of AD and age-gender matched control samples obtained from a commercial source (Precision Med). Set 3 contained 4 each of AD and age-gender matched controls obtained from second commercial source (BioReclamation).

As shown in FIG. 3A-E, we found >15 subjects with levels higher than our detection limit for all 5 analytes. In set 3, the levels of TE, sNDE, cNDE in AD were less than paired controls, whereas these values were slightly higher in AD than paired controls in set 1. Because of 2 distinct populations, we then calculated the incidence of subjects exceeding the upper detection limit (FIG. 3, a-e). Both control and AD samples showed 15-25% beyond the upper limit, whereas MCI samples resulted in 50% above the upper limit. Using non-parametric Mann-Whitney test, the incidence of MCI in ODE was significantly (p<0.05) higher than that of controls.

Figure 7:
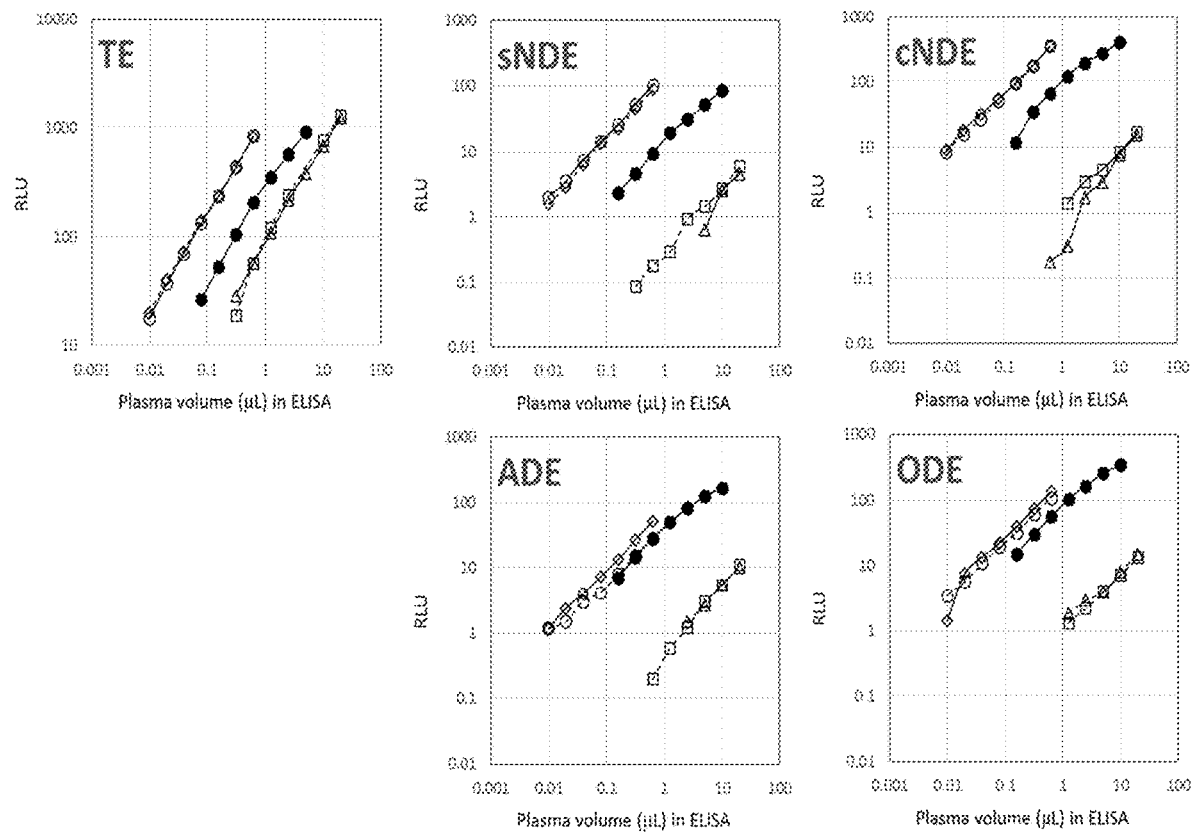
FIG. 7 sets forth data showing plasma dilution studies of low, medium, and high quantity of exosomes.

The values in FIG. 3 were re-analyzed in X-Y plots. As shown in FIG. 4, the levels of sNDE and cNDE were well correlated with the values of total exosomes. This may indicate that the quantity of NDE is large enough to influence the calculation of total exosomes. Interestingly, the values of sNDE and cNDE were very close with an $r^2=0.991$, whereas the values of NDE were very different from those of ADE and ODE, indicating that NDE, ADE, ODE are different targets As shown in FIG. 3, levels of TE, sNDE, cNDE, ADE, and ODE demonstrated two distinct groups, one group within our detection range and the other group exceeding the upper detection limits. The high values were attributable to technical issues, because the variation between duplicate samples was very small as shown in FIG. 2. Such high values were reproduced in the second experiment (FIG. 2F). Plasma dilution of such subjects demonstrated a reduction (FIG. 7) in values within range. Brain exosomes are known to spread and propagate pathology to neighboring regions and such over-production of exosomes will be a prime research focus in the future. Because MCI showed significantly more high values (FIG. 3E) than control, this may be related to the predisposition to further development of cognitive impairment or AD.

Figure 8A:
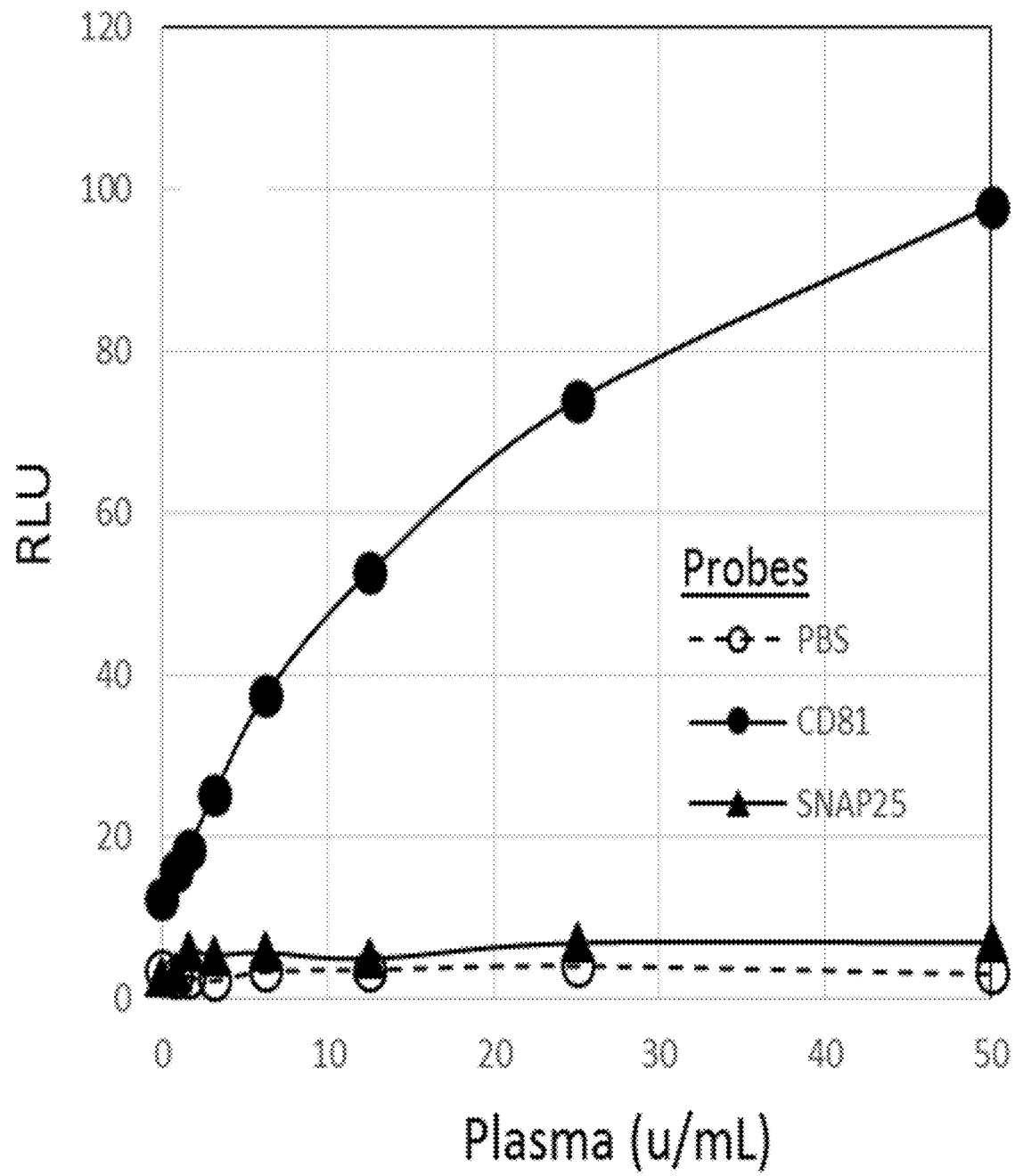
FIGS. 8A and 8B set forth data showing difference between sNDE and cNDEs. Various volumes of plasma were applied to anti-CD171- (A) or anti-SNAP25-immobilized ELISA wells (B), followed by the reaction with biotinylated anti-CD81 and PBS as a positive and negative control as well as biotinylated anti-SNAP25 (A) or anti-CD171 antibodies (B).
Figure 8B:
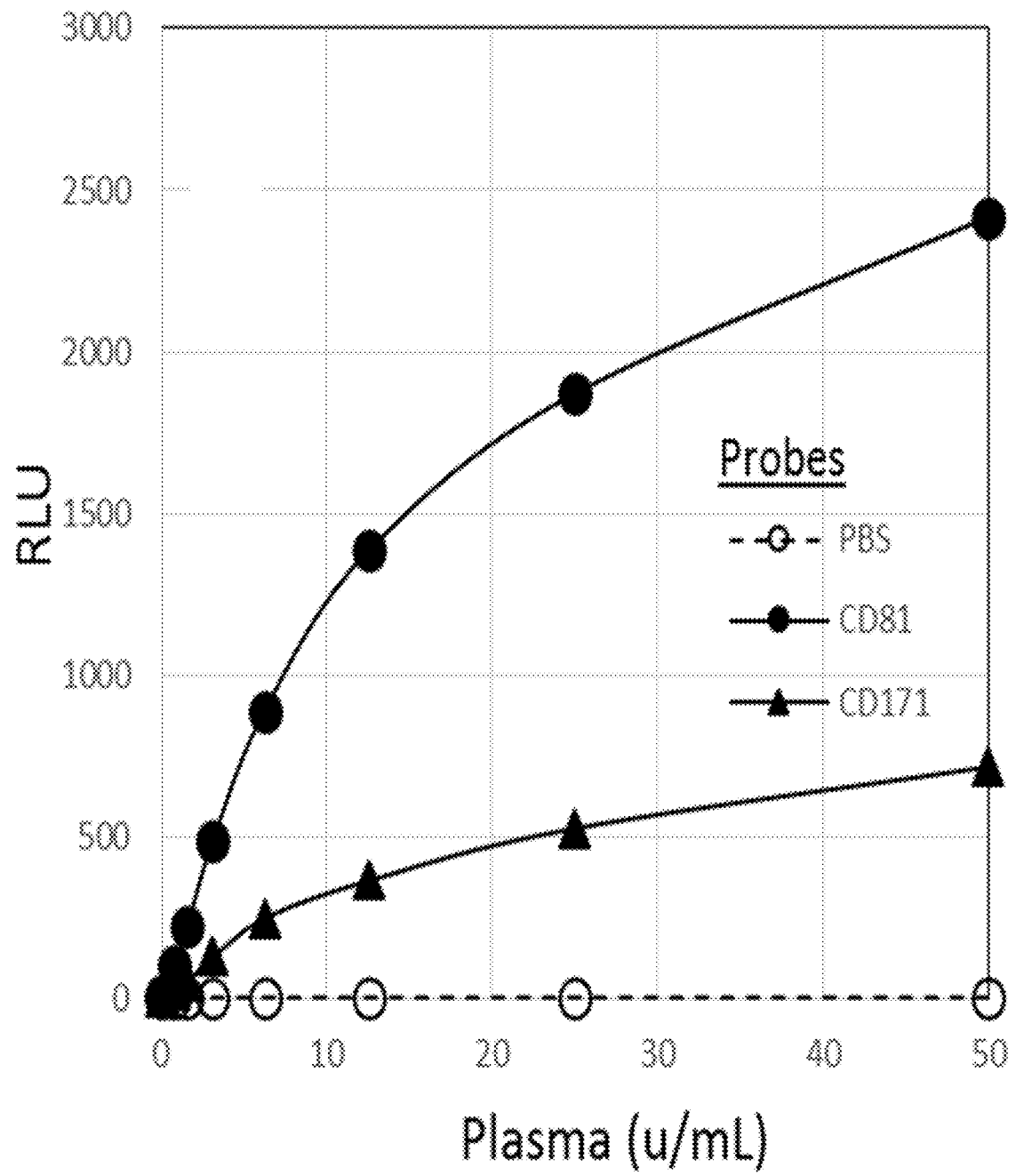

We analyzed correlation among analytes as shown in FIG. 4. The levels of sNDE and cNDE closely correlated as indicated by an $r^2=0.991$. As shown in FIG. 8, CD171 was detected on anti-SNAP25-immobilized ELISA strips, whereas SNAP25 was extremely low in anti-CD171-immobilized ELISA strips. In our preliminary studies, we isolated sNDE and cNDE, respectively, and found that the amounts of tau protein were much higher in cNDE than sNDE (data not shown). Thus, these two NDEs are not identical. However, the values of these two types of NDEs were different from those of ADE and ODE, indicating that NDE, ADE, and ODE are looking at different targets.

These results showed that the methods and compositions of the present invention are useful for isolating and quantifying exosomes and specific subpopulations of exosomes. These results further showed that methods and compositions of the present invention are useful for identifying subjects with neurodegenerative disorders. These results further indicated that methods and biomarkers of the present invention are useful for diagnosing neurodegenerative disorders. These results suggested that methods of the present invention would be useful for treating subjects with neurodegenerative disorders.

Example 2: Isolation and Quantification of Subpopulations of Exosomes from Biological Samples Specific subpopulations of exosomes were isolated and quantified from biological samples as follows. ELISA assays were performed using white ELISA plates (Coster, Corning, NY), ELISA coating buffer, and ELISA wash buffer (BioLegend, San Diego, CA). Various antibodies and control mouse IgG were immobilized onto ELISA plates. After pooled human plasma was applied to the ELISA plates, captured exosomes were incubated with anti-CD81 antibody (BD Pharmigen, San Jose, CA).

Figure 9:
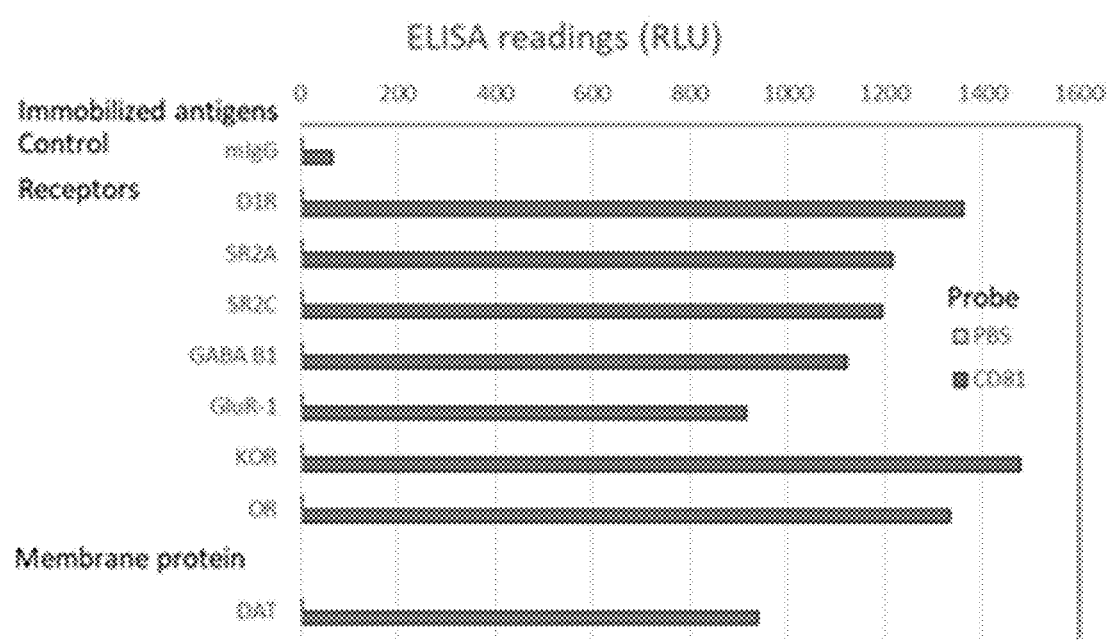
FIG. 9 sets forth data showing neural biomarkers of the present invention can be used to detect and isolate exosomes from plasma.

As shown in FIG. 9, antibodies against various neurotransmitter receptors were positive, which included dopamine receptor 1 (DR1), serotonin receptor 2A (SR2A) and 2C (SR2C), gamma-aminobutyric acid (GABA) B1 receptor, glutamate receptor-1 (GluR-1), opioid receptor (KOR), and sleep peptide orexin receptor (OR). Dopamine transporter (DAT) is a membrane protein present on the presynaptic dopaminergic neurons, and this also showed increased signal with anti-CD81 (see FIG. 9).

These results showed that methods and compositions of the present invention are useful for isolating and quantifying exosomes and specific subpopulations of pre-synaptic dopaminergic neuron-derived exosomes, or post-synaptic dopaminergic, serotonergic. GABAnergic, glutamatergic, and opioid neuron-derived exosomes. These results further showed that the methods and biomarkers of the present invention are useful for isolating and quantifying exosomes and specific subpopulations of exosomes, including, for example, neural-derived exosomes.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method comprising, simultaneously detecting double positive exosomes in a biological sample, wherein the exosomes are positive for one or more exosome biomarkers selected from the group consisting of CD81, CD63, and CD9 and wherein the exosomes are positive for one or more neural biomarkers selected from the group consisting of CD171, SNAP25, EAAT1, and OMGP, thereby simultaneously detecting double positive exosomes in the sample.

2. The method of claim 1, wherein the one or more neural biomarkers are selected from the group consisting of a dopamine receptor, a serotonin receptor, a GABA receptor, a glutamate receptor, an opioid receptor, an orexin receptor, an adrenalin receptor, a noradrenalin receptor, an acetylcholine receptor, and a dopamine receptor.

3. The method of claim 1, further comprising capturing the exosomes on a solid support comprising at least one capture reagent attached thereto, wherein the capture reagents bind at least one biomarker selected from the group consisting of CD81, CD63, and CD9.

4. The method of claim 1, further comprising capturing the exosomes on a solid support comprising at least one capture reagent attached thereto, wherein the capture reagents bid at least one biomarker selected from the group consisting of a dopamine receptor, a serotonin receptor, a GABA receptor, a glutamate receptor, an opioid receptor, an orexin receptor, an adrenalin receptor, a noradrenalin receptor, an acetylcholine receptor, and a dopamine transporter.

5. The method of claim 1, further comprising capturing the exosomes on a solid support comprising at least one capture reagent attached thereto, wherein the capture reagents bind at least one biomarker selected from the group consisting of SNAP25, EAATI, OMGP, DR1, SR2A, SR2C, GABAB1, GluR-1, KOR, OR, or DAT.

6. The method of claim 1, wherein the exosomes are selected from the group consisting of neuron-derived exosomes, astrocyte-derived exosomes, oligodendrocyte-derived exosomes, and microglia-derived exosomes.

7. The method of claim 1, wherein the biological sample is selected from the group consisting of whole blood, serum, plasma, urine, interstitial fluid, peritoneal fluid, cervical swab, tears, saliva, buccal swab, skin, brain tissue, and cerebrospinal fluid.

* * * * *